United States Patent
Czerney et al.

(10) Patent No.: US 6,924,372 B2
(45) Date of Patent: Aug. 2, 2005

(54) BENZOPYRYLO-POLYMETHINE-BASED HYDROPHILIC MARKERS

(75) Inventors: Peter Czerney, Weimar (DE); Matthias Wenzel, Jena (DE); Bernd Schweder, Jena (DE); Wilhelm Frank, Jena (DE)

(73) Assignee: Dyomics GmbH, Jena (DE)

( * ) Notice: Subject to any disclaimer, the term of this patent is extended or adjusted under 35 U.S.C. 154(b) by 0 days.

(21) Appl. No.: 10/732,928

(22) Filed: Dec. 10, 2003

(65) Prior Publication Data

US 2004/0162423 A1 Aug. 19, 2004

(30) Foreign Application Priority Data

Dec. 10, 2002 (DE) .......................................... 102 58 150

(51) Int. Cl.[7] .............................................. C09B 23/02
(52) U.S. Cl. ......................... 546/71; 546/101; 548/454
(58) Field of Search ................... 546/71, 101; 548/454; 435/92, 93, 172, 800

(56) References Cited

U.S. PATENT DOCUMENTS 6,143,434 A * 11/2000 Okada ........................ 428/690
2002/0115862 A1 * 8/2002 Czerney et al. ............... 546/89

FOREIGN PATENT DOCUMENTS

DE          199 11 421      10/2000
WO          WO 00/53678      3/1999

OTHER PUBLICATIONS

Czerney et al., Biological Chemistry, 382(3), 495–498, 2001.*

U.S. Appl. No. 09/700,072, Czerney et al., filed Feb. 2, 2001.

* cited by examiner

*Primary Examiner*—Fiona T. Powers
(74) *Attorney, Agent, or Firm*—Kirkpatrick & Lockhart Nicholson Graham LLP

(57) ABSTRACT

The present invention relates to the field of optical-fluorescent markers, particularly to benzopyrylo-polymethine-based optical-fluorescent markers.

1 Claim, 24 Drawing Sheets

BENZOPYRYLO-POLYMETHINE-BASED HYDROPHILIC MARKERS

Figure 1:
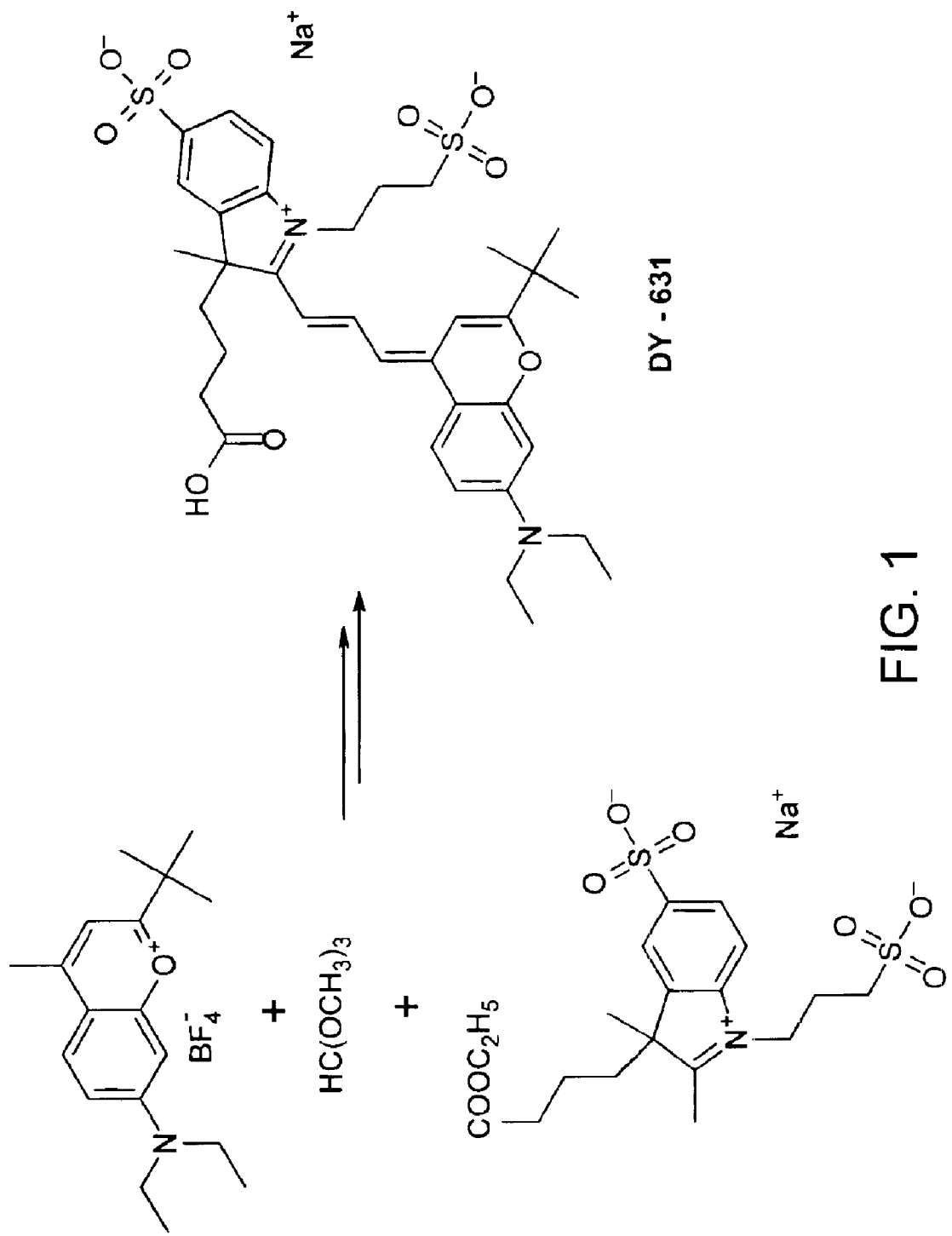

This application claims priority under 35 U.S.C. § 119(a) to German Patent Application No. DE 102 58 150.9, filed on Dec. 10, 2002, the entire disclosure of which is incorporated by reference herein.

The invention is concerned with benzopyrylo-polymethine-based markers for use in optical, and in particular optical-fluorescent, determination and detection procedures, for example in medicine, the pharmaceutical industry and in bioscience, materials science and environmental science.

The challenge was to create highly hydrophilic content polymethine-based fluorescent markers with high extinction coefficients and a high degree of photo and storage stability. These can be excited simply to emit fluorescent light by monochromatic (laser/laser diodes) or polychromatic light (white light sources) in the UV, visual or NIR spectrum range or can function as quenchers.

For the purposes of the invention, general formula I and/or II polymethine-based chromophores are used.

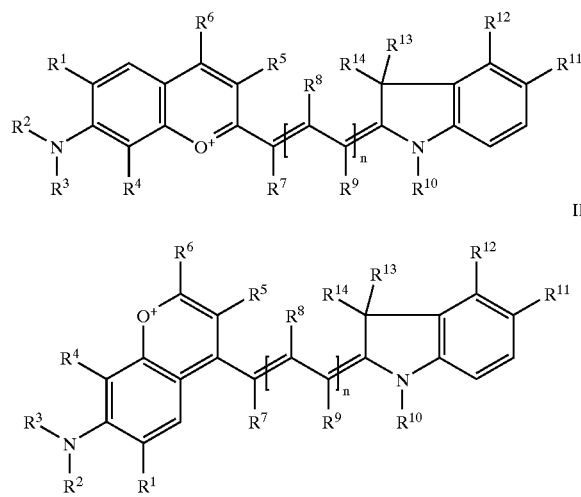

The invention covers the use as markers of appropriate asymmetrical polymethine-based hydrophilic complexes and their application in optical and in particular optical fluorescent, determination and detection procedures.

Typical applications are based on the reaction of dye-marked biomolecules such as, for example, antigens, antibodies or DNA segments, in each case with the complementary species, enabling, inter alia, enzyme kinetics, receptor-ligand interactions and nucleic acid hybridization kinetics to be measured both in vitro and in vivo. Furthermore, the markers are interesting from the point of view of the pharmacological characterization of receptors or active materials.

Accordingly, opportunities for their use exist in, for example, medicine and the pharmaceutical industry, bioscience, materials science, environmental monitoring and the detection of organic and inorganic micro-specimens occurring in nature and the world of technology and in other areas as well.

Symmetrical xanthylium salt (fluoresceine and rhodamine) or polymethine (indocynanine) as claimed in, for example, U.S. Pat. No. 5,627,027 are normally used.

All these markers have the disadvantage that they tend towards aggregation and dimerization owing to the planarity of the π-electron system, especially in aqueous systems. Moreover, insufficiently hydrophilic markers show non-specific interactions with different surfaces, resulting in problems with cleaning the corresponding conjugates and in an unsatisfactory signal/noise ratio.

In order to circumvent these disadvantages, corresponding asymmetrical polymethines on the basis of benzob]pyran-2-ylide or benzo[b]pyran-4-ylide-compounds were described in patent specifications PCT/DE OO/00802 and PCT/DE O1/01946.

We were then able to improve these markers even further by introducing additional substituents which increased the level of marker hydrophily.

New general formula I and/or II polymethine-based hydrophil markers are now the subject of the invention,

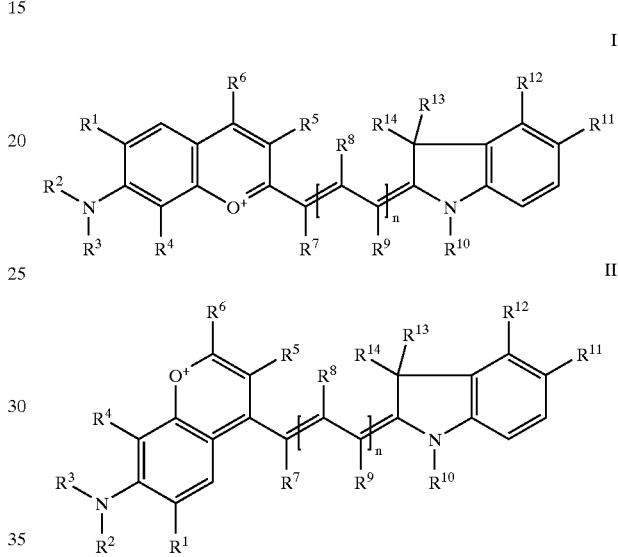

where
$R^1$–$R^4$ are the same or different and may be hydrogen, alkyl-, tert-alkyl, aryl-, carboxyaryl-, dicarboxyaryl, heteroaryl-, cycloalkyl-, heterocycloalkyl-, alkyloxy-, alkylmercapto- (with "alkyl" and "cycloalkyl" also including olefin linkage residues), aryloxy-, arylmercapto-, heteroaryloxy-, heteroarylmercapto-, hydroxy-, nitro- or cyano residues and $R^1$ und $R^2$, $R^2$ and $R^3$, $R^3$ and $R^4$, $R^5$ and $R^7$, $R^9$ and $R^{10}$, $R^{11}$ and $R^{12}$ or $R^{12}$ and $R^{13}$ may form one or more aliphatic, heteroaliphatic or aromatic rings,
at least one or more of the $R^1$–$R^{14}$ substituents may constitute solubilizing or ionizing or ionized substituents such as $SO_3^-$, $PO_3^{2-}$, $CO_2H$, OH, $NR_3^+$, cyclodextrines or sugars, which determine the hydrophil characteristics of dyes; these substituents may also be linked to the actual basic chromophore by means of an aliphatic or heteroaliphatic or cyclical spacer group, as the case may be,
at least one of the $R^1$–$R^{14}$ substituents stands for a reactive group of the isocyanate, isothiocyanate, hydrazine, amin, mono- and dichlor- or mono- and dibromtriazine, aziridine, sulfonylhalogenide, N-hydroxysuccinimidester, imido-ester, glyoxal or aldehyde or maleimide or Iodacetamide and phosphoramidite type; the substituent in question may be linked to the actual basic chromophore by means of an aliphatic or heteroaliphatic or cyclical spacer group, as the case may be,
the aliphatic or heteroaliphatic spacer group consists of a structural element —[$(CH_2)_a$—Y—$(CH_2)_b$]$_c$—, in which Y—the same or different—may be a $CR_2$—, O—, S—, $SO_2$, $SO_2NH$—, NR—, COO— or CONR function, with R assuming the functions of $R^1$–$R^{14}$ and a and b—the same or different—representing values 0–18 and c values 1–18, n stands for numerical values 0, 1, 2 or 3; substituents $R^8$ and $R^9$—doubled or threefold to give n=2 or 3 respectively—may be the same or different.

The complexes covered by the invention ("invention complexes") may be used as dyes for the optical marking of proteins, nucleic acids, oligomers, DNA, RNA, biological cells, lipids, mono-, oligo- and polysaccharids, ligands, receptors, polymers, pharmaceutical or polymer particles and coupled via the functional groups to an HO—, $H_2N$—, HS or $HO_2C$ function of the substances to be determined, as dyes used in systems determining the quality or quantity of proteins, nucleic acids, oligomers, DNA, RNA, biological cells, lipids, polymers, pharmaceutical or polymer particles.

This coupling reaction is achieved to advantage in organic or aqueous solutions.

The conjugates from the invention complexes and biomolecules display fluorescing characteristics or deactivate the activated state without emitting light (quencher).

The invention complexes have an application in qualitative and quantitative optical and in particular optical fluorescent, determination procedures, including immune tests, hybridization procedures, chromatographic or electrophoretic procedures, FRET systems and high-throughput screening or for the analysis of receptor-ligand change effects on a microarray. General formula I and/or II polymethines may be used as dyes for optical marking of organic or inorganic identification units, such as, for example, aminoacids, peptides, proteins, antigens, haptens, enzyme substrates, enzyme co-factors, biotins, carotinoids, hormones, neuro-hormones, neuro-transmitters, growth factors, lympholocines, lectins, toxins, carbohydrates, oligosaccharides, polysaccharides, dextrans, nucleic acids, oligonucleotides, DNA, RNA, biological cells, lipids, receptor-linking pharmaceutical or organic or inorganic polymer carriers.

Marking of identification units can be done by the the formation of ionic interactions occurring between the general formula I and/or II complexes and the materials to be marked.

The identification unit or carrier can also be linked covalently with the fluorophore. This coupling reaction can be achieved in an aqueous or mainly aqueous solution, preferably at room temperature. The resulting probe (conjugate) determines the quality or quantity of different bio-materials or other organic and inorganic materials through the use of optical procedures.

Both general formula I and/or II complexes and derived systems can be used in qualitative and quantitative optical, and in particular optical fluorescent, determination procedures for diagnosing cell characteristics (molecular imaging), biosensors (point of care measurements), genome research and miniaturization technologies. Typical applications occur in cytometry and cell sorting, fluorescence correlation spectroscopy (FCS), Ultra-High-Throughput-Screening (UHTS), multicolor fluorescence in-situ hybridization (FISH), FRET systems and microarrays (DNA- and protein chips).

A microarray is a grid arrangement of molecules immobilized on at least one surface which can be used for the study of receptor-ligand change effects. A grid arrangement denotes more than two differing surface molecules which are immobilized in known positions in varying pre-defined regions of the surface.

A receptor is a molecule which has an affity to a given ligand. Receptors can be naturally occurring or synthetically produced molecules. They can be used in pure form or in association with another species. They can be linked covalently or non-covalently to a linkage partner either directly or by means of certain coupling mediators.

Examples of receptors which are detectable on the basis of this invention include agonists and antagonists for cell membrane receptors, toxins and other poisonous substances, viral epitopes, hormones such as opiates and steroids, hormone receptors, peptides, enzymes, enzyme substrates, active substances acting as co-factors, lectines, sugars, oligonucleotides, nucleic acids, oligosaccharides, cells, cell fragments, tissue fragments, proteins and antibodies. However, they are not limited to these substances.

A ligand is a molecule which is recognized by a certain receptor. Examples of ligands which are detectable by means of the invention compounds include agonists and antagonists for cell membrane receptors, toxins and other poisonous substances, viral epitopes, hormones such as opiates and steroids, hormone receptors, peptides, enzymes, enzyme substrates, active substances acting as co-factors, lectines, sugars, oligonucleotides, nucleic acids, oligosaccharides, proteins and antibodies. However, they are not limited to these substances.

The following advantages are achieved by the preparation of asymmetrical polymethines posessing, on the one hand, an easily derivatizable heterocycle selected from CH acidic compounds as a terminal function and, on the other, a 6 ring heterocycle (novel substitution).

Already relatively small molecules absorb in the spectral range over 550 nm and display fundamentally improved photochemical and thermal stability compared with previously known polymethines with maximum absorption maxima above 650 nm (penta- and heptamethines).

It is possible, through molecular engineering, to control the position and intensity of absorption and emission maxima at will and to adjust them in line with emission wavelengths of different activating lasers, in particular diode lasers.

The invention complexes are comparatively simply to manufacture by condensing the two different CH-acid heterocycles and a C-1, C-3 or C-5 component ("mulligan procedure").

Further manufacturing procedures involve condensation of one of the CH acid heterocycles with the C-1, C-3 or C-5 component at an initial reaction stage and—following the isolation of the 1:1 condensation product—conversion to a polymethine with the second CH-acid heterocycle in a subsequent condensation process. The sequence of heterocycle applications involved is not inconsiderable. On the basis thereof, many heavily hydrophilic, variously functionalized dyes differing in respect of total charge and the specificity/reactivity of the activated groups used for the purposes of immobilization can be easily manufactured in few reaction steps.

The examples shown below in the drawing should provide a more detailed explanation of the invention.

FIG. 1: Synthesis of DY-631

Example 1

Figure 2:
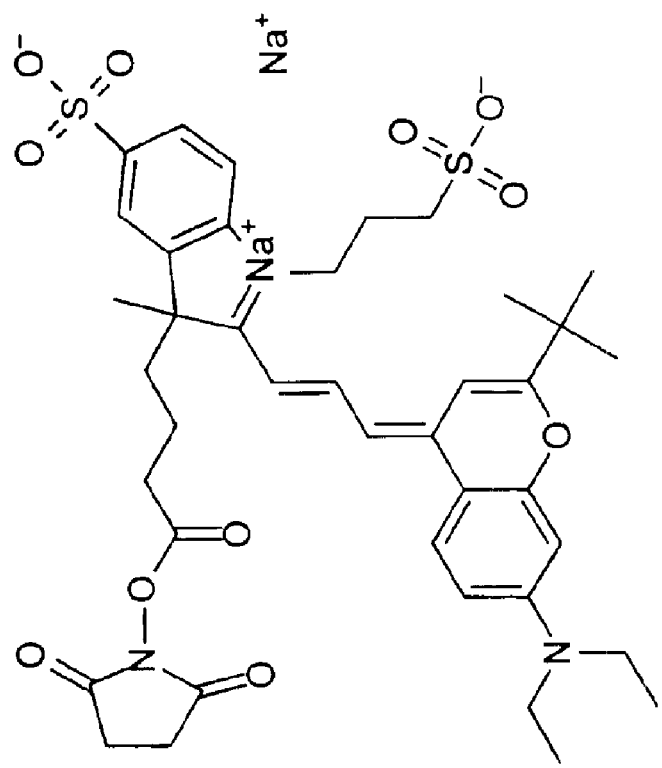
Figure 2:
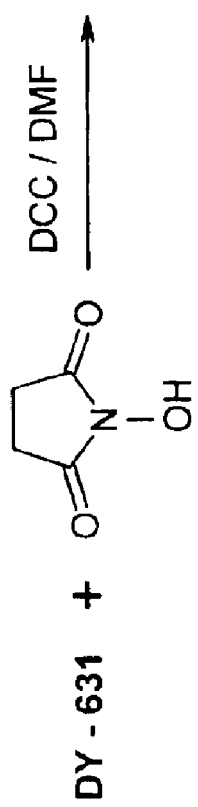

FIG. 2: Synthesis of DY-631 N-Hydroxysuccinimidyl ester

Example 2

Figure 3:
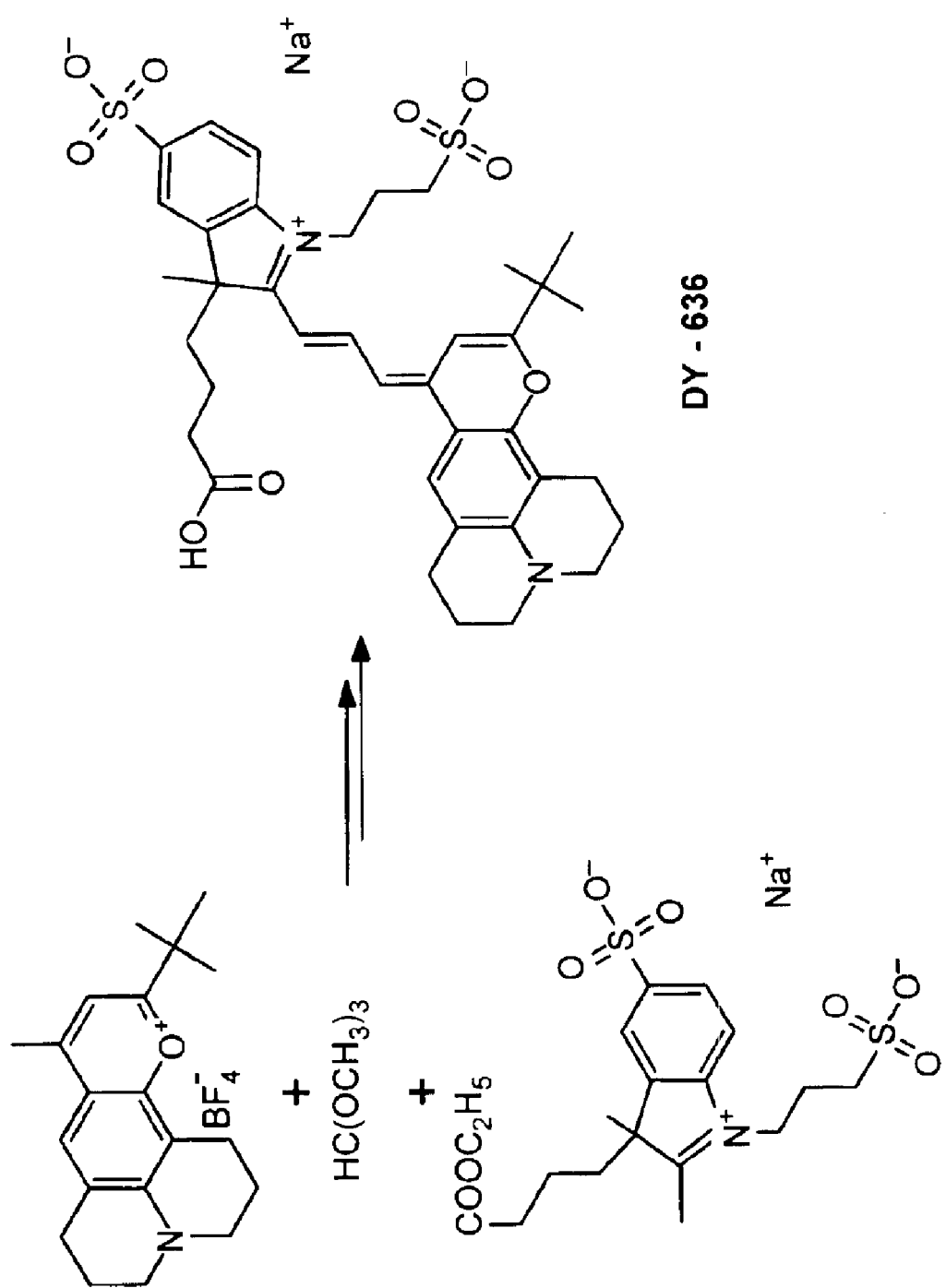

FIG. 3: Synthesis of DY-636

Example 3

Figure 4:
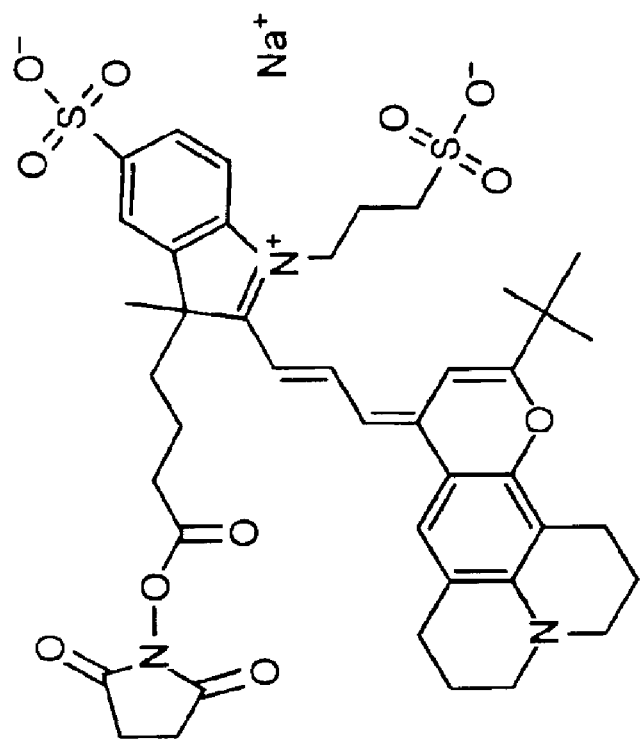
Figure 4:
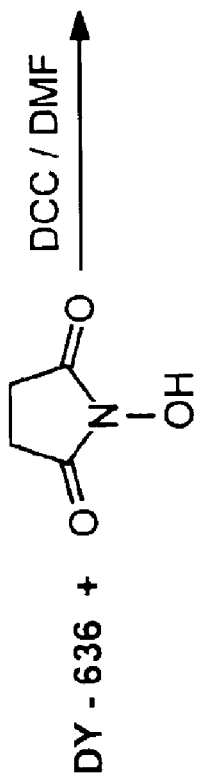

FIG. 4: Synthesis of DY-636 N-Hydroxysuccinimidyl ester

Example 4

Figure 5:
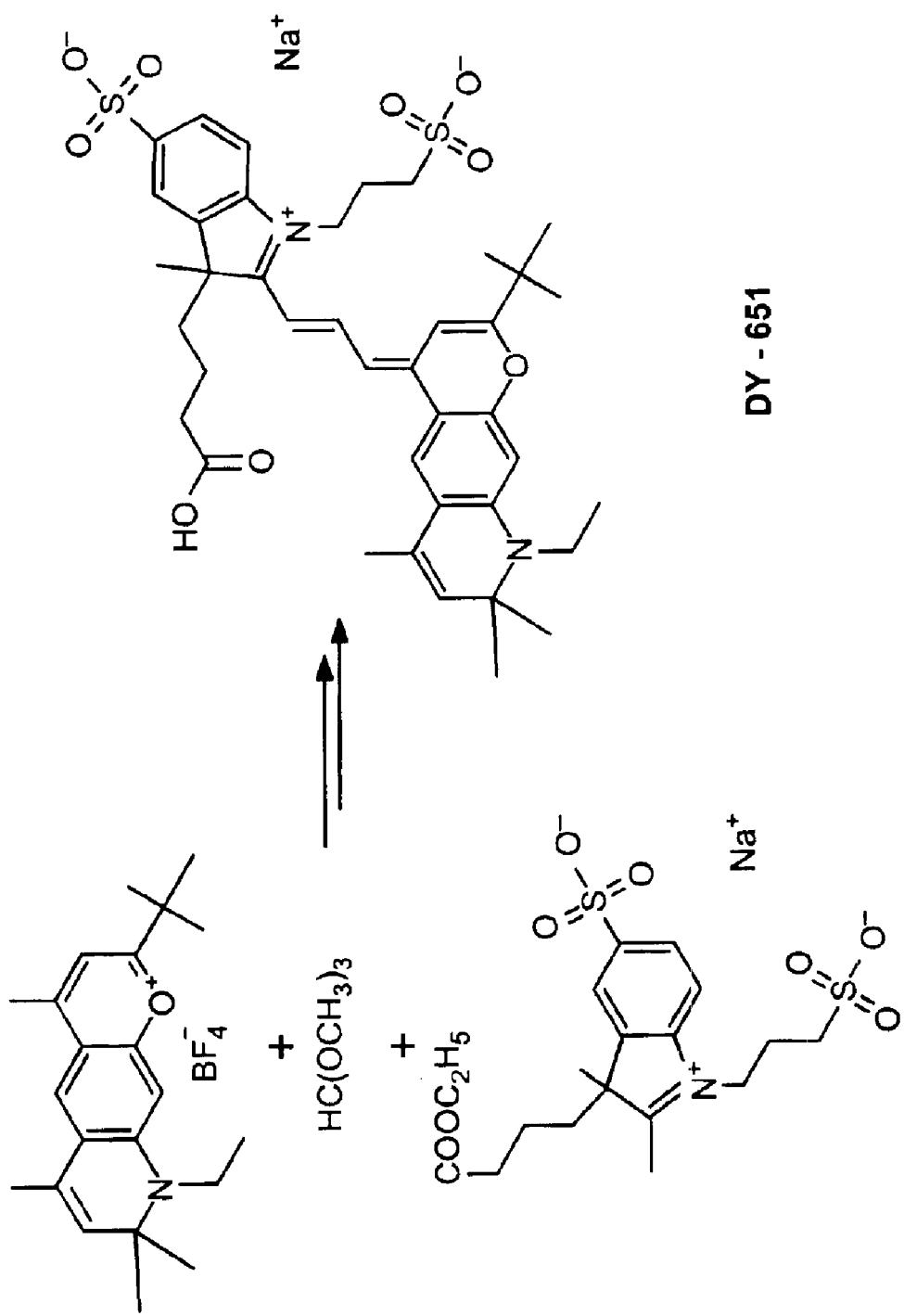

FIG. 5: Synthesis of DY-651

Example 5

Figure 6:
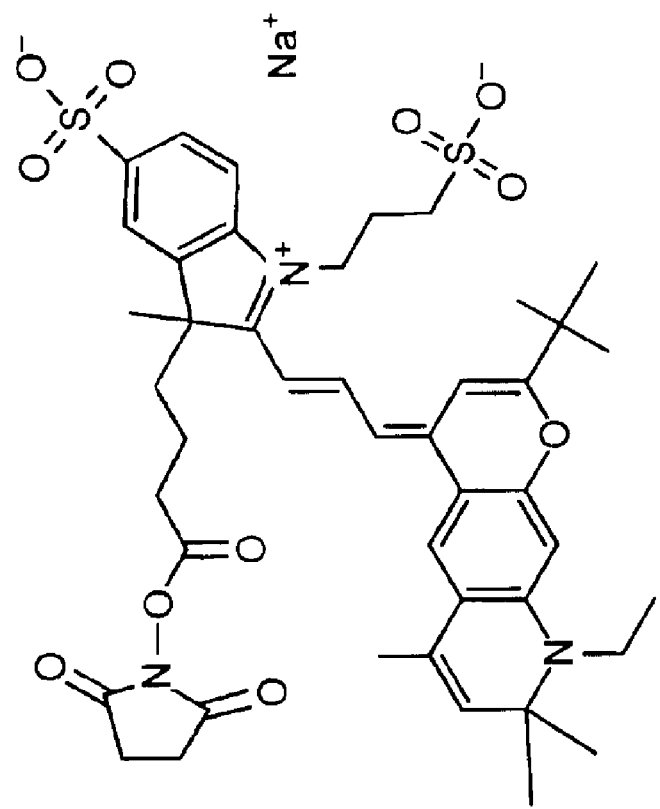
Figure 6:
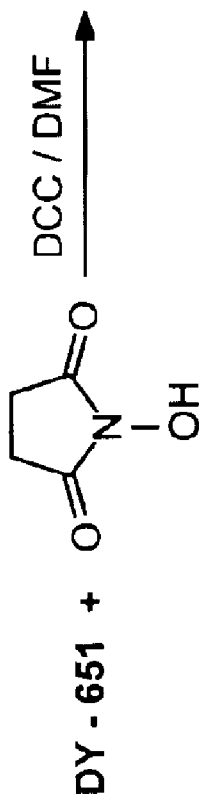

FIG. 6: Synthesis of DY-651 N-Hydroxysuccinimidyl ester

Example 6

Figure 7:
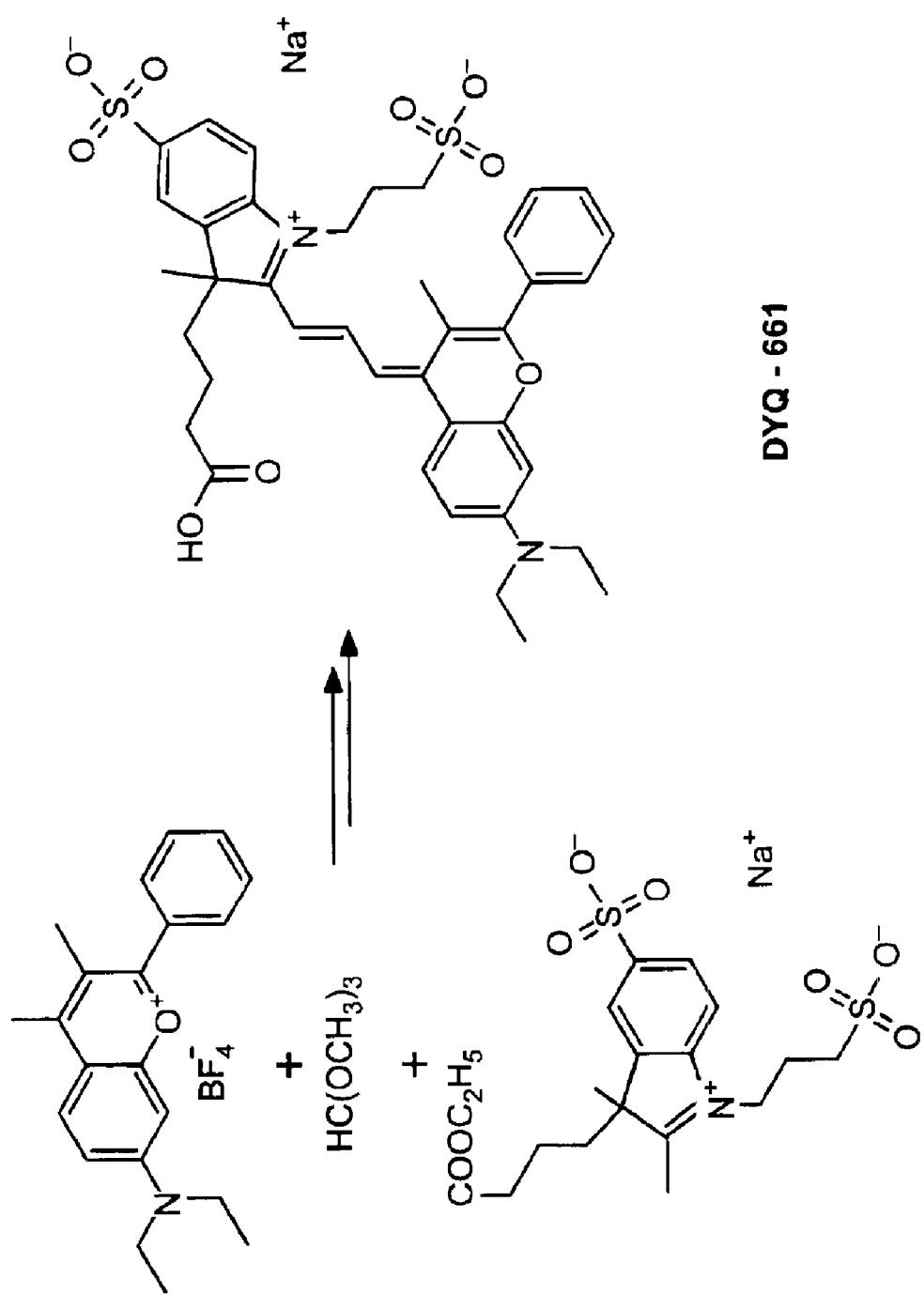

FIG. 7: Synthesis of DYQ-661

Example 7

Figure 8:
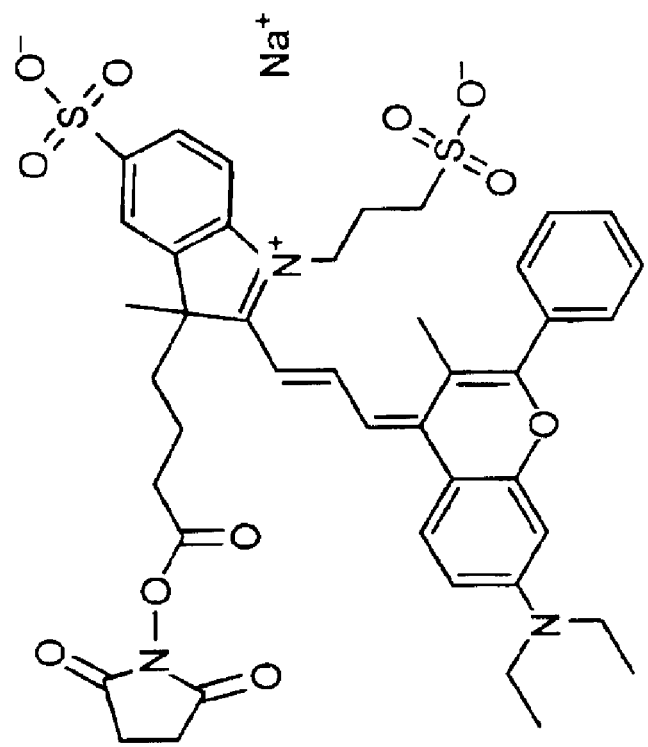
Figure 8:
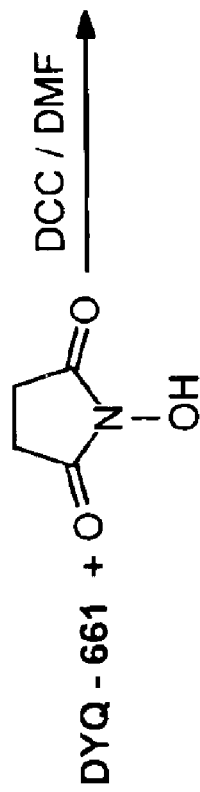

FIG. 8: Synthesis of DYQ-661 N-Hydroxysuccinimidyl ester

Example 8

Figure 9:
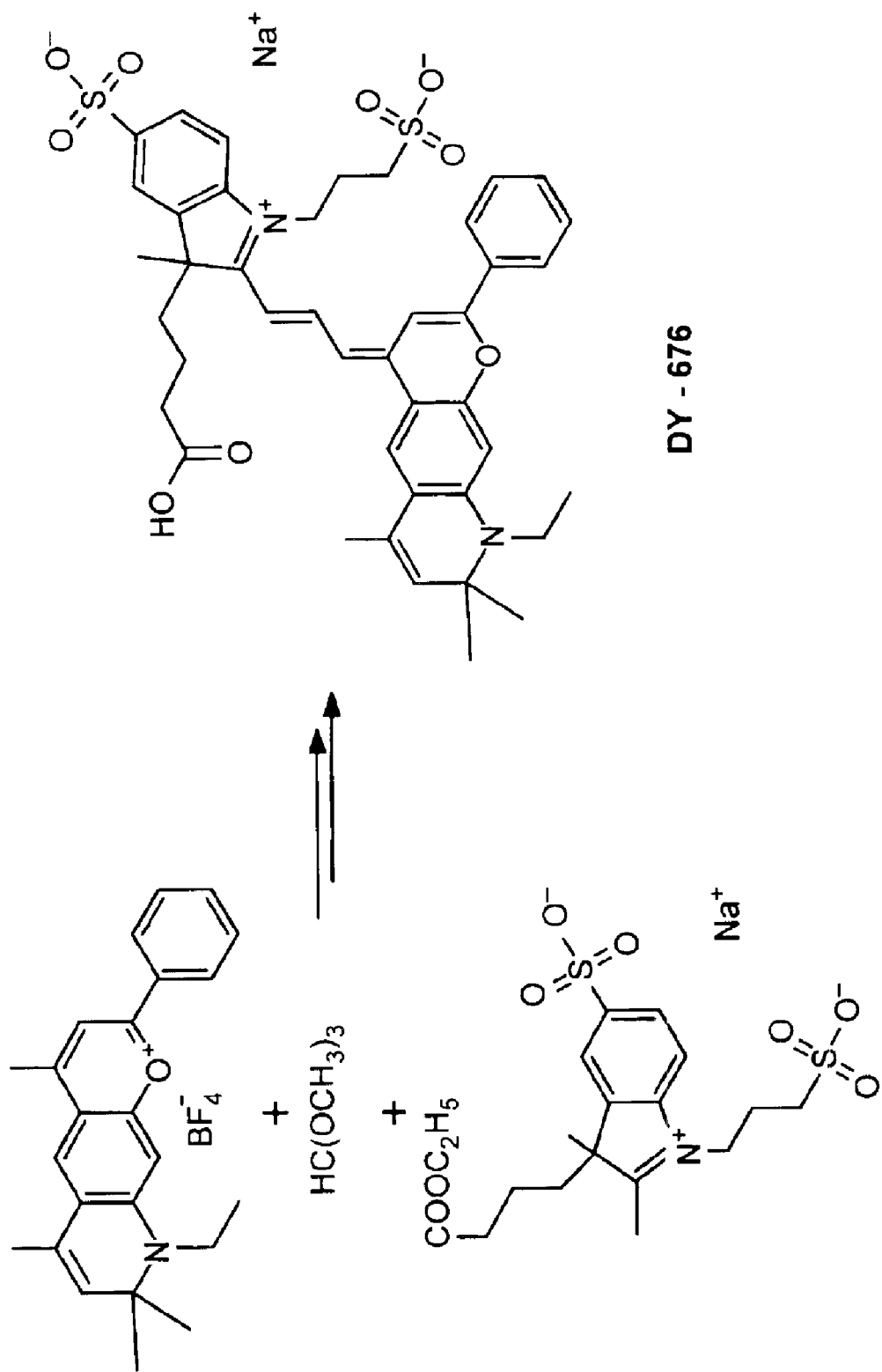

FIG. 9: Synthesis of DY-676

Example 9

Figure 10:
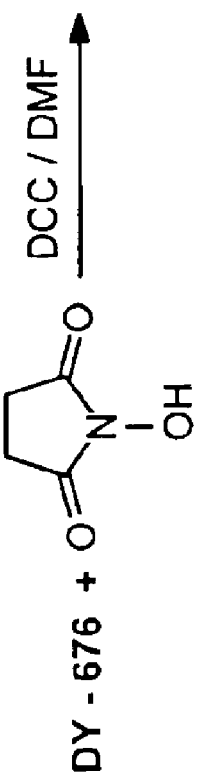
Figure 10:
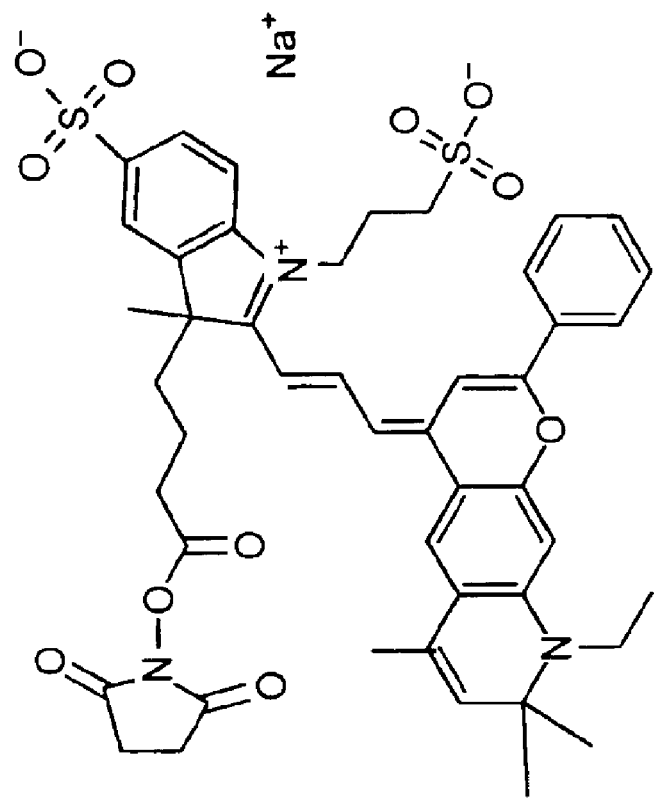

FIG. 10: Synthesis of DY-676 N-Hydroxysuccinimidyl ester

Example 10

Figure 11:
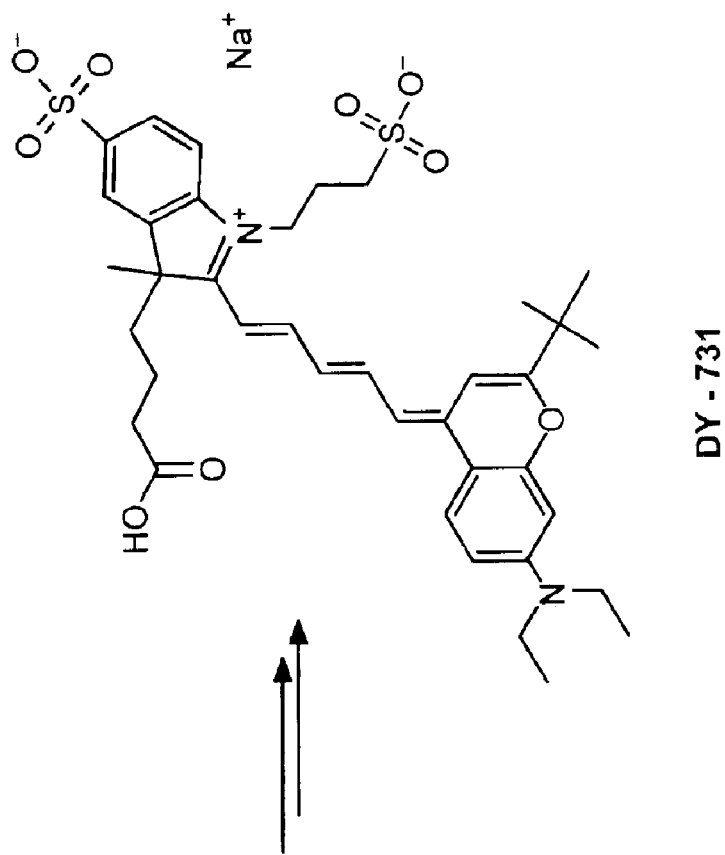
Figure 11:
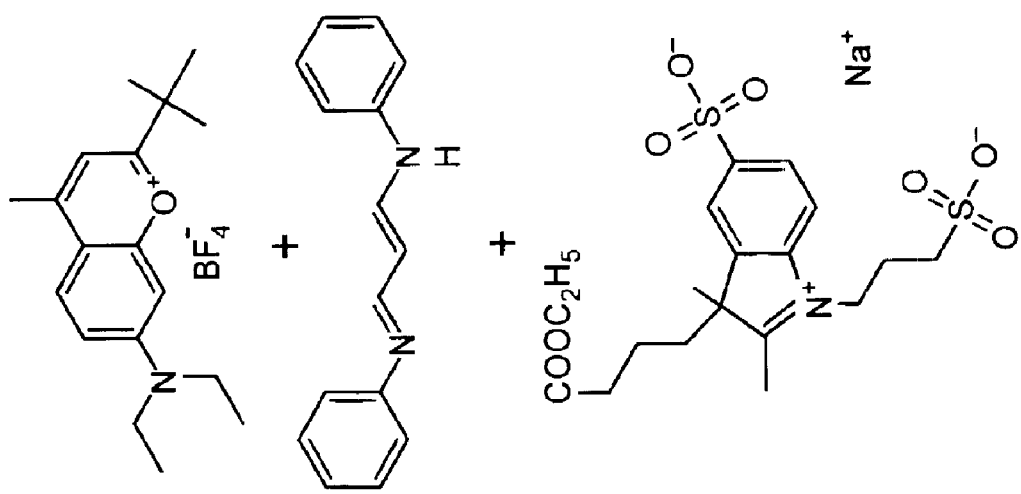

FIG. 11: Synthesis of DY-731

Example 11

Figure 12:
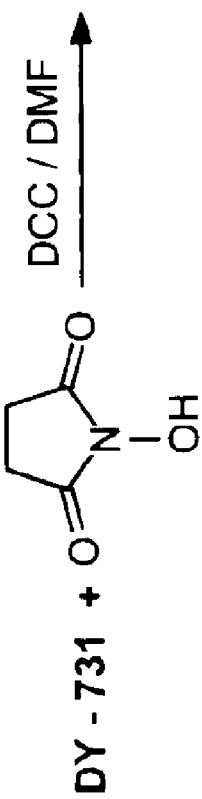
Figure 12:
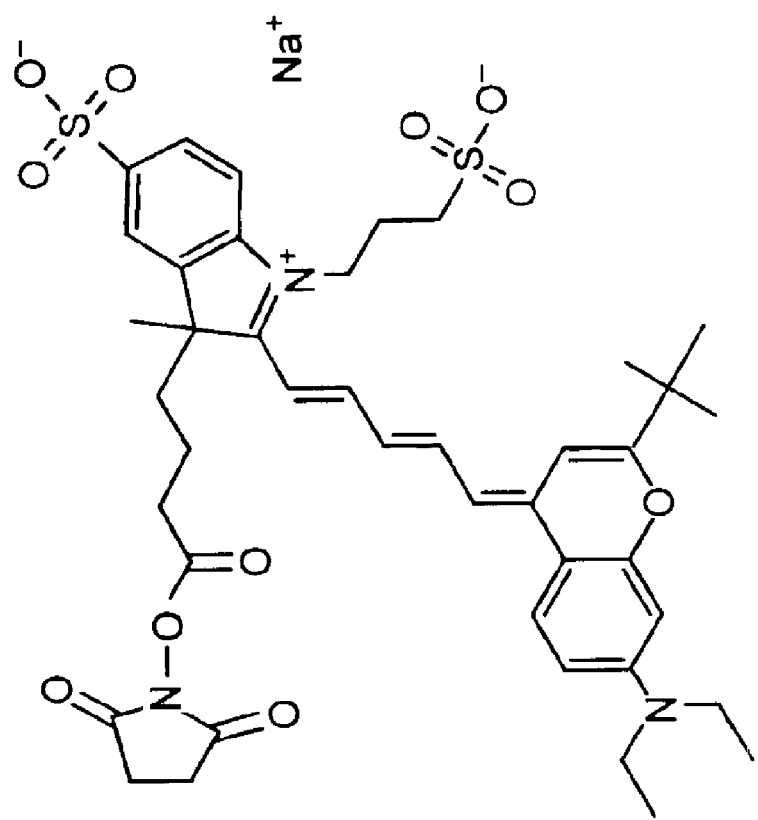

FIG. 12: Synthesis of DY-731 N-Hydroxysuccinimidyl ester

Example 12

Figure 13:
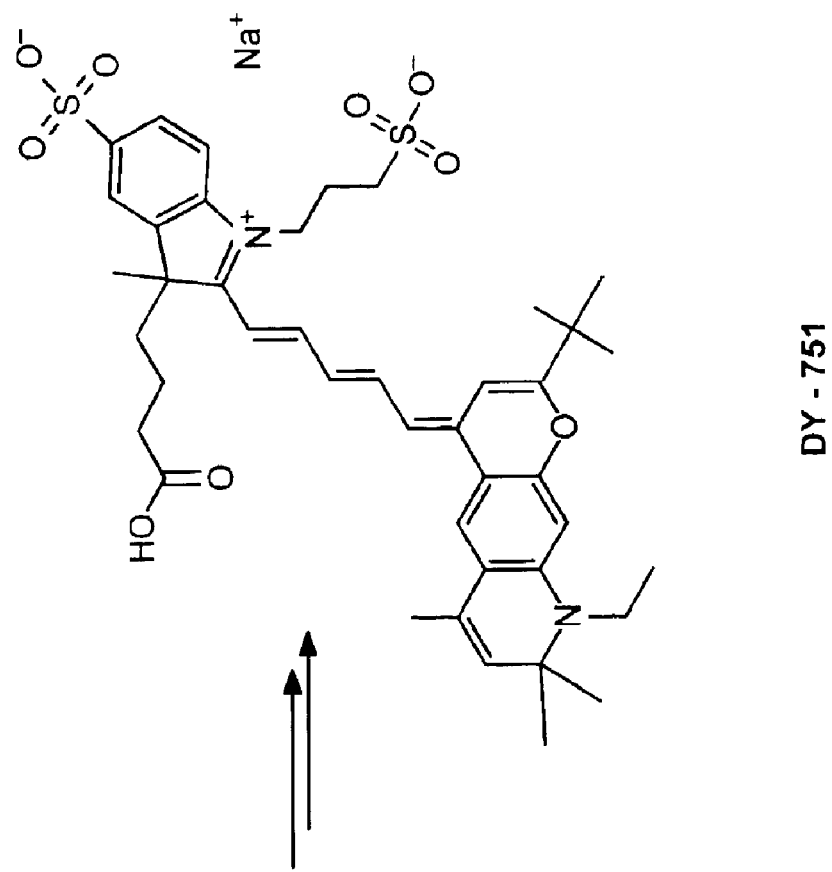
Figure 13:
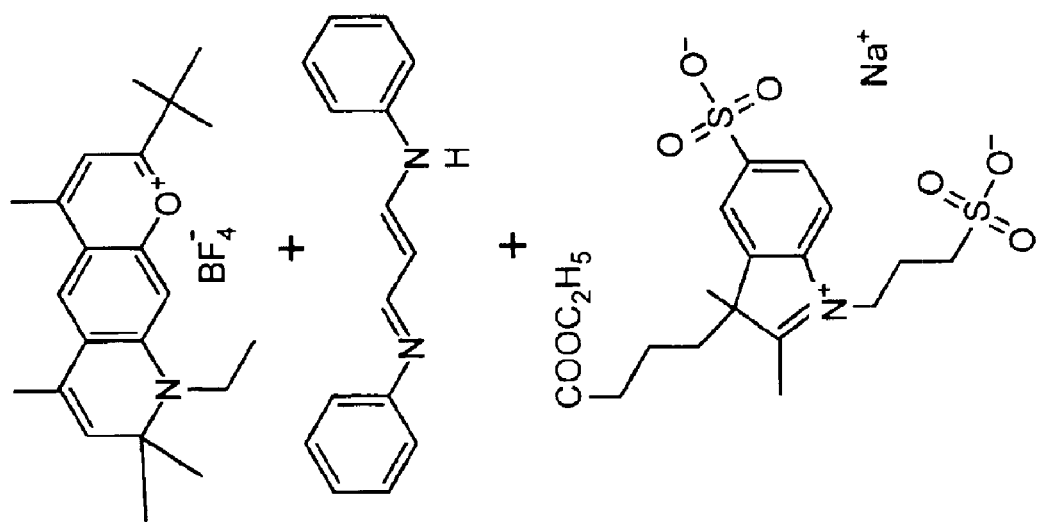

FIG. 13: Synthesis of DY-751

Example 13

Figure 14:
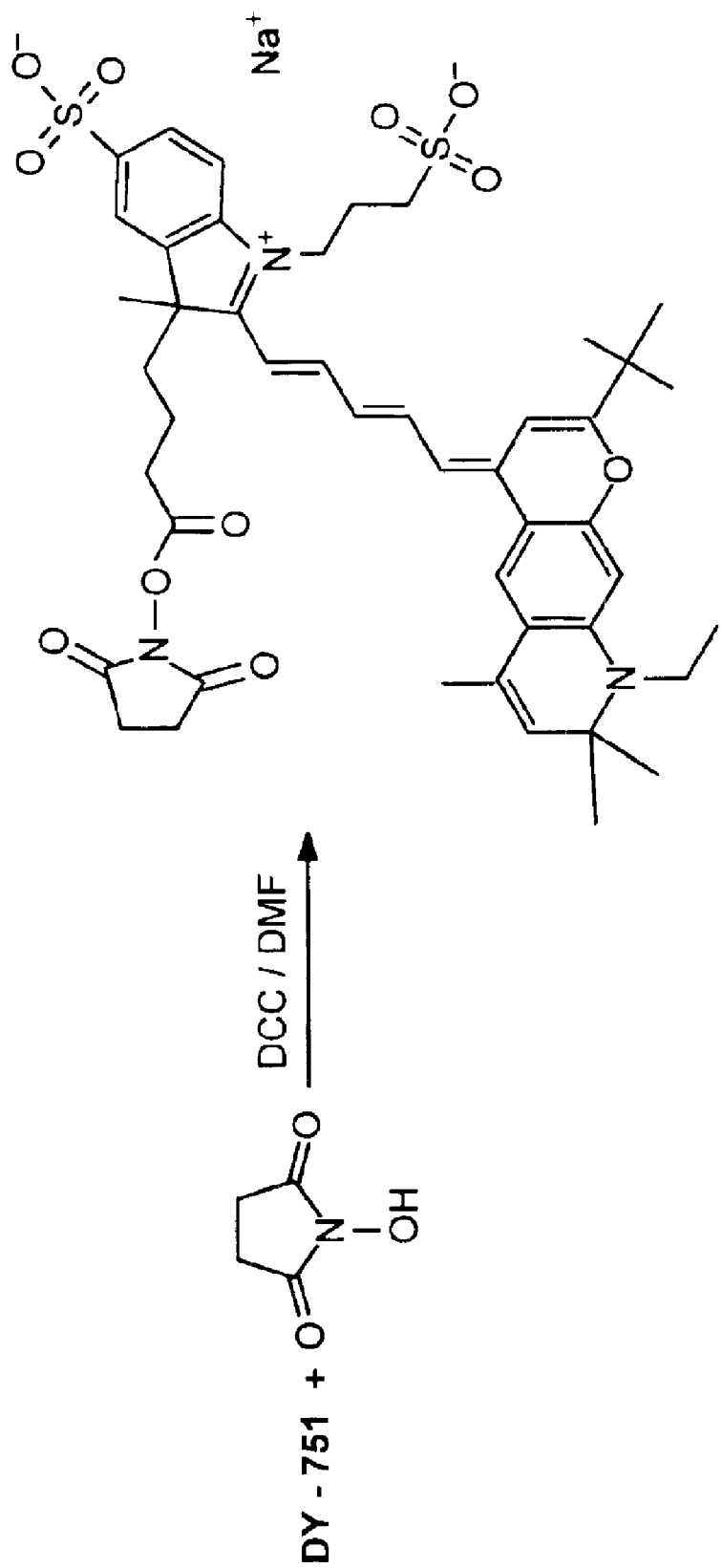

FIG. 14: Synthesis of DY-751 N-Hydroxysuccinimidyl ester

Example 14

Figure 15:
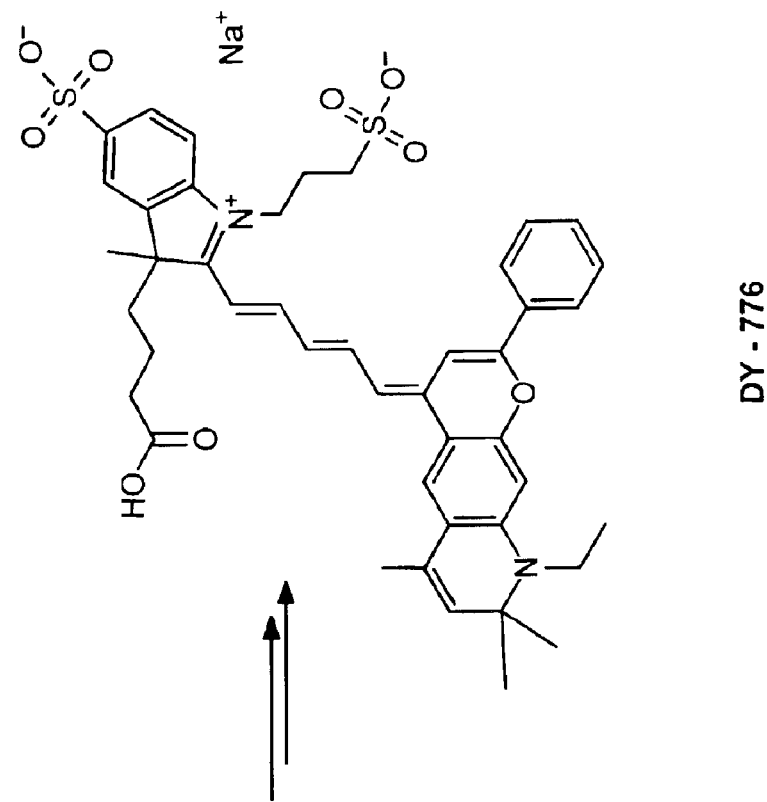
Figure 15:
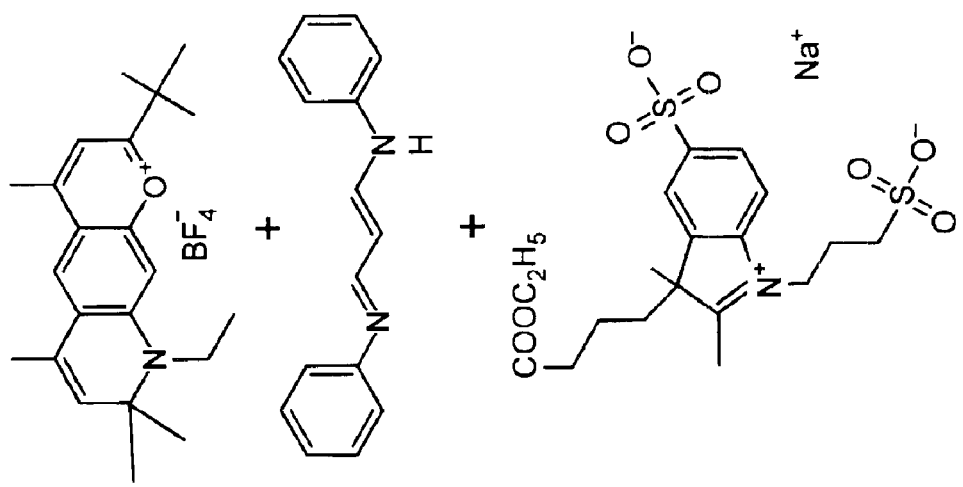

FIG. 15: Synthesis of DY-776

Example 15

Figure 16:
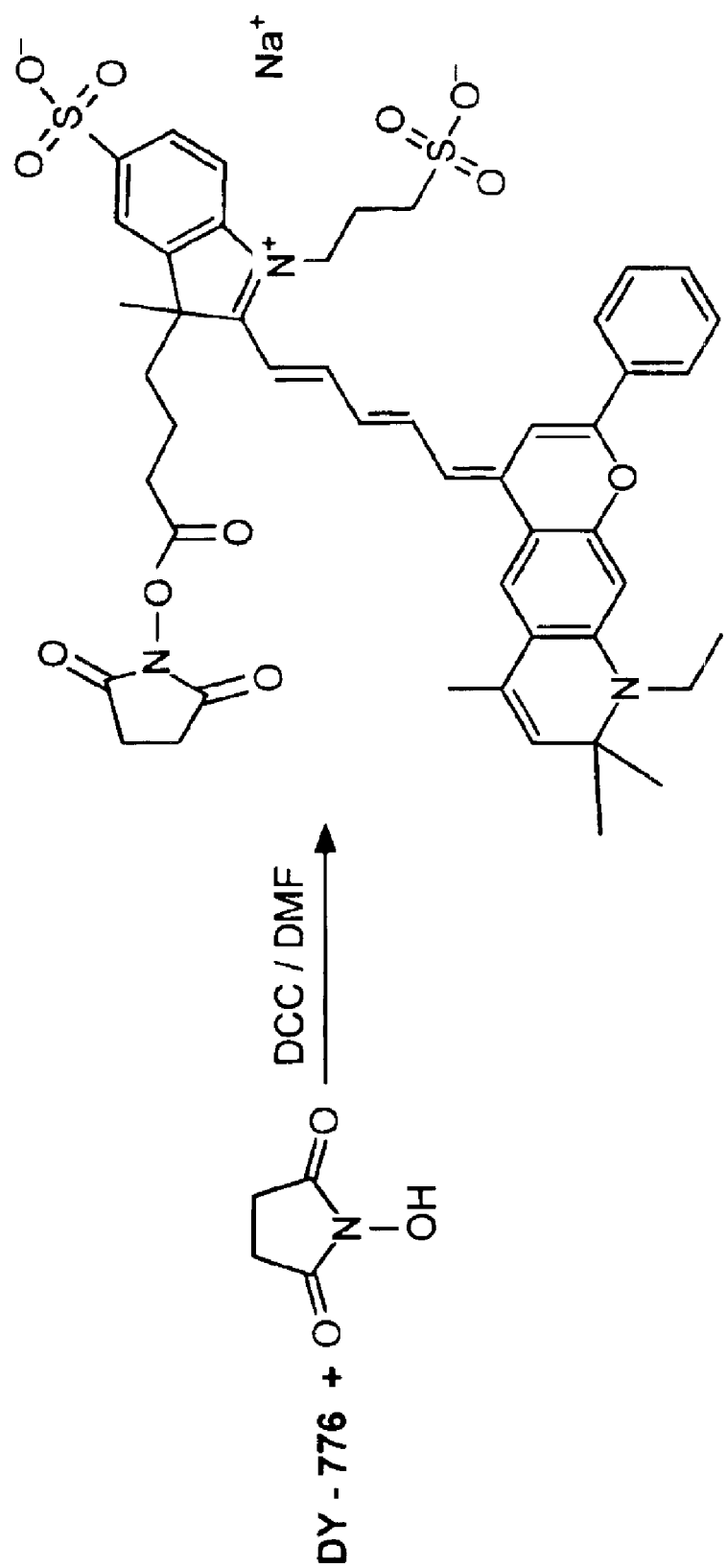

FIG. 16: Synthesis of DY-776 N-Hydroxysuccinimidyl ester

Example 16

Figure 17:
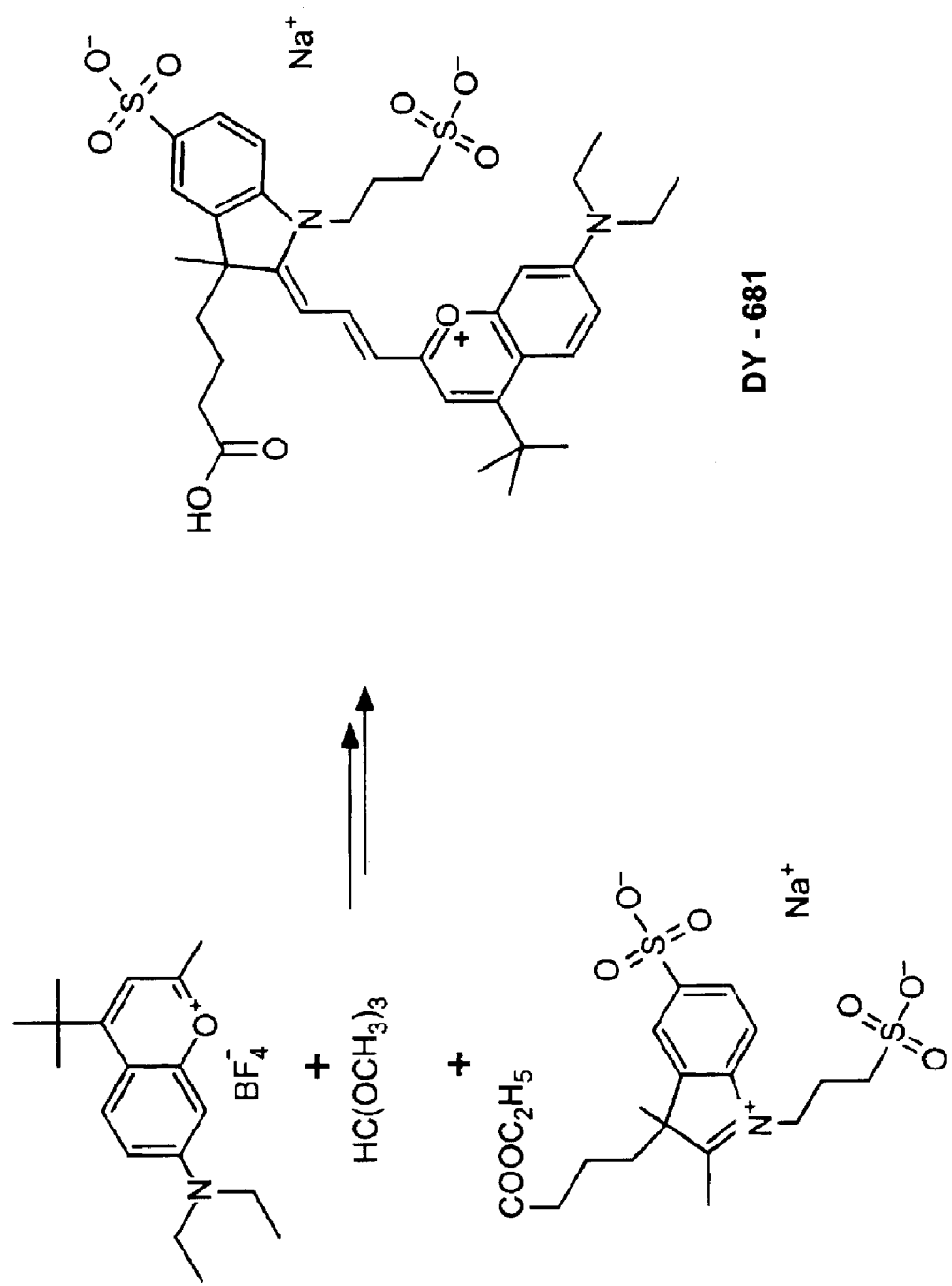

FIG. 17: Synthesis of DY-681

Example 17

Figure 18:
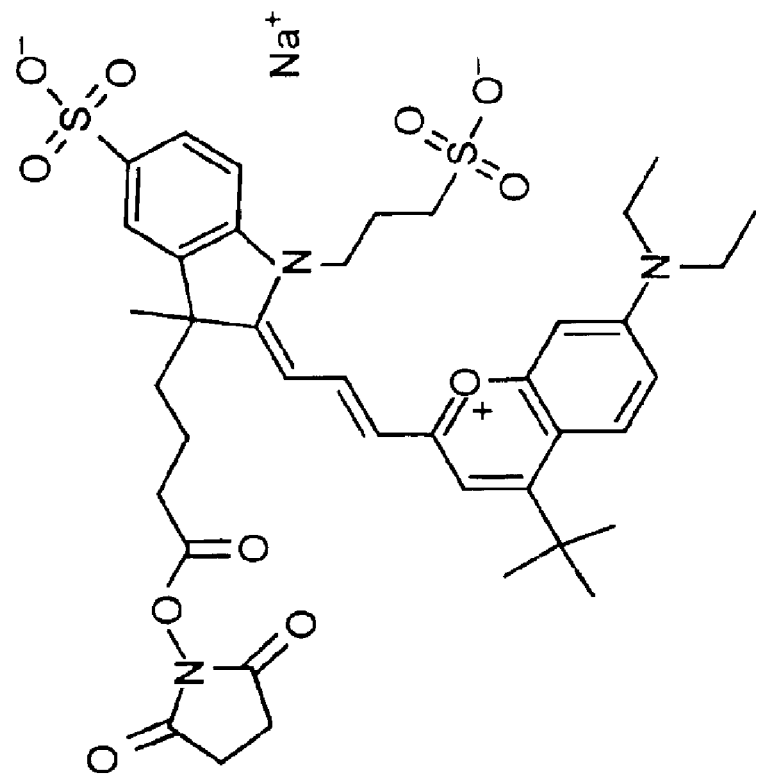
Figure 18:
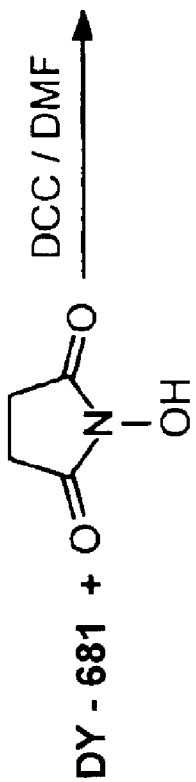

FIG. 18: Synthesis of DY-681 N-Hydroxysuccinimidyl ester

Example 18

Figure 19:
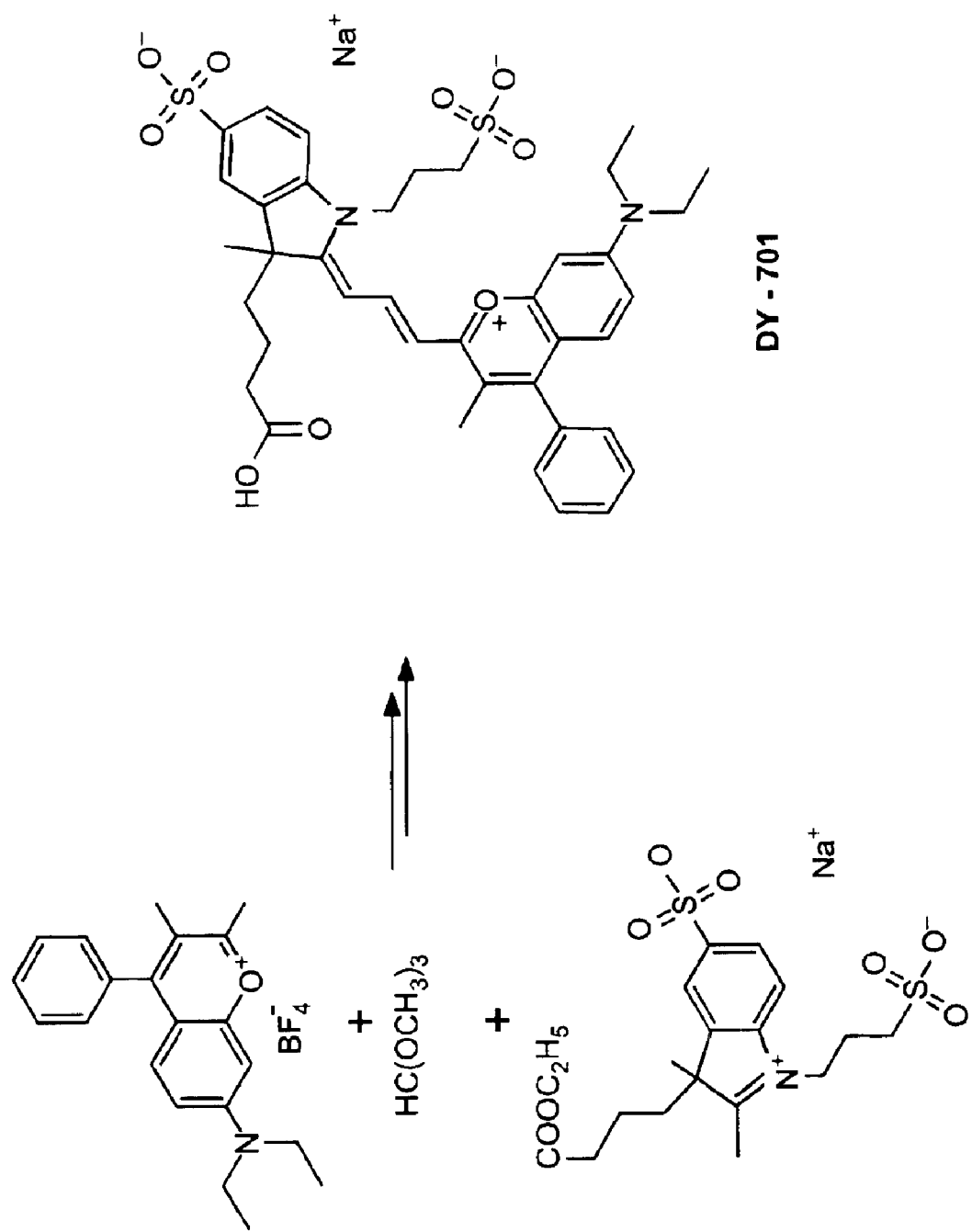

FIG. 19: Synthesis of DY-701

Example 19

Figure 20:
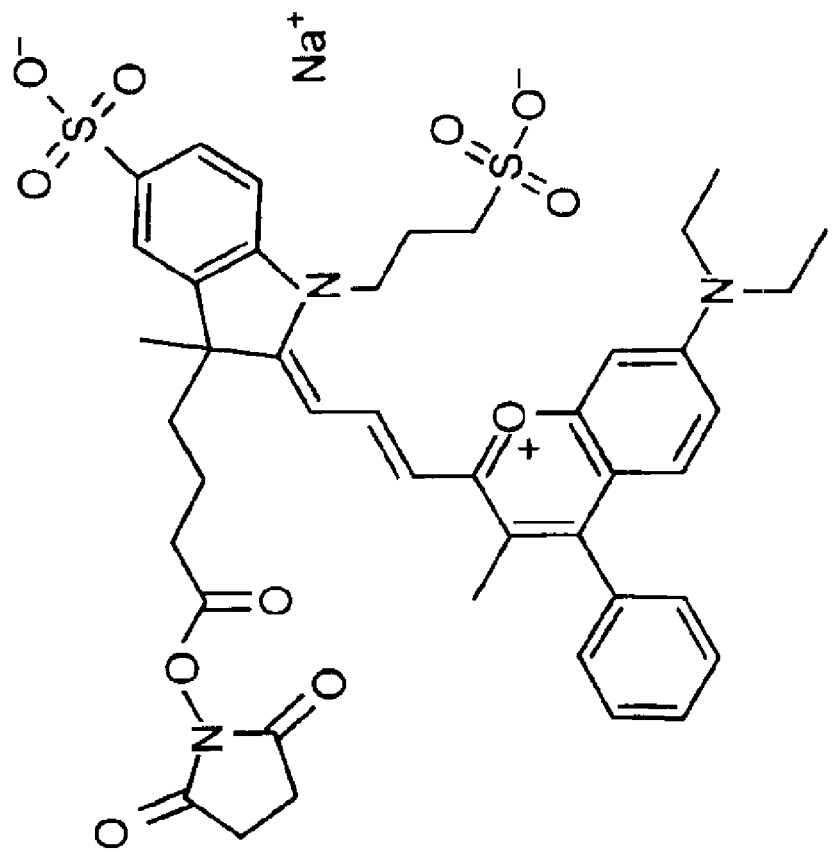
Figure 20:
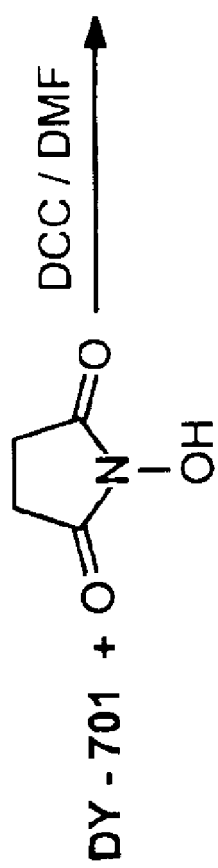

FIG. 20: Synthesis of DY-701 N-Hydroxysuccinimidyl ester

Example 20

Figure 21:
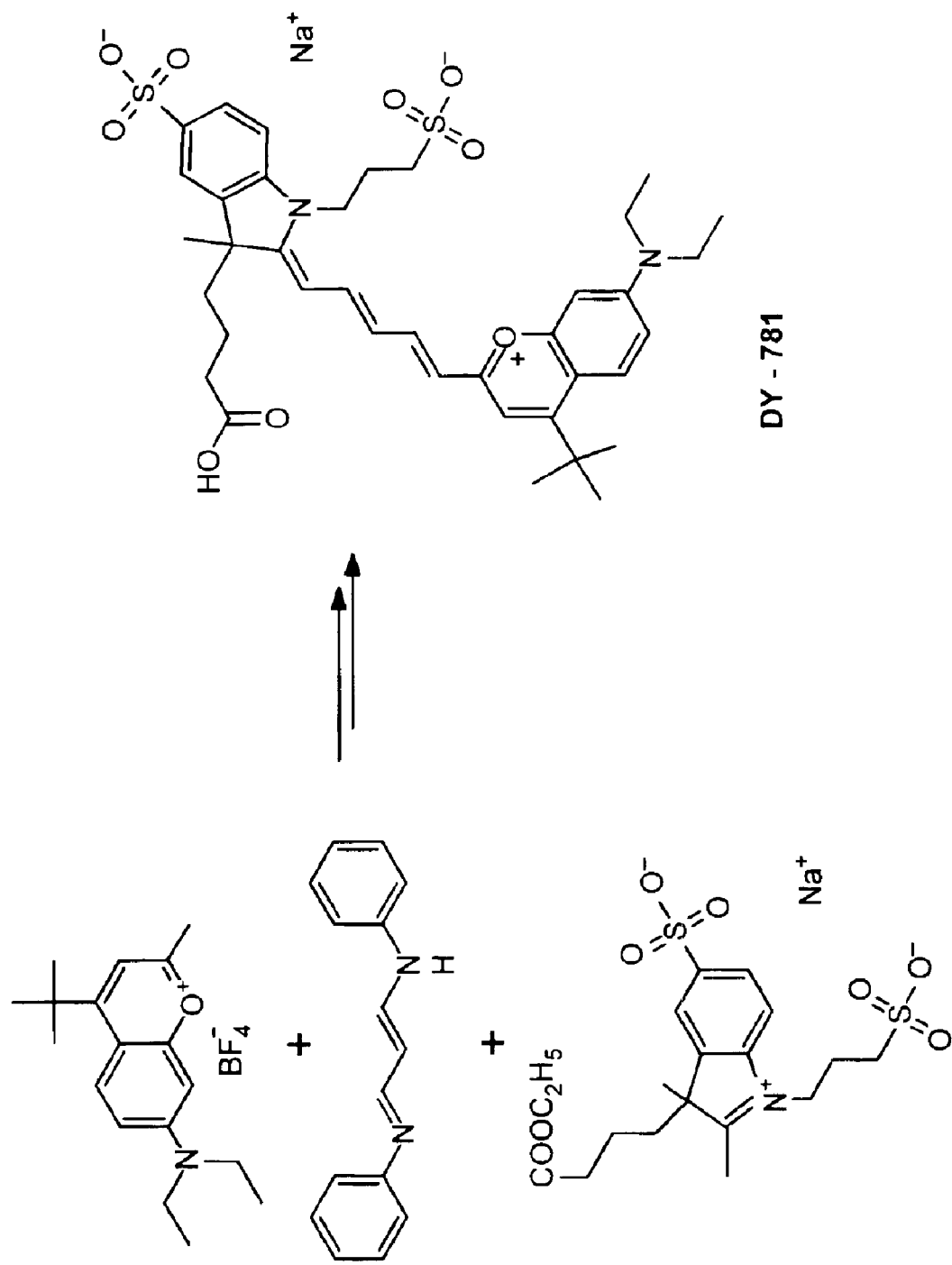

FIG. 21: Composition of DY-781

Example 21

Figure 22:
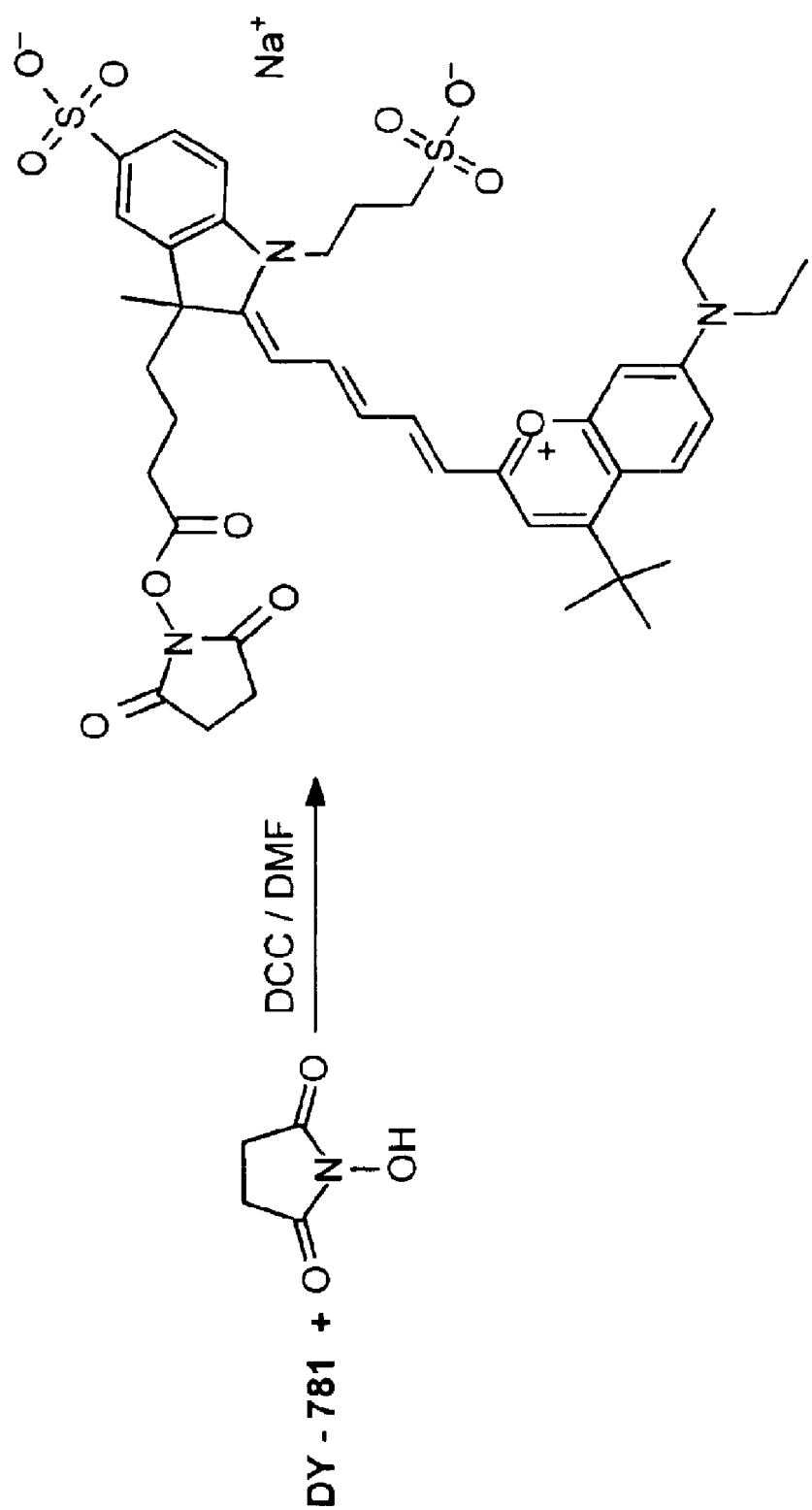

FIG. 22: Synthesis of DY-781 N-Hydroxysuccinimidyl ester

Example 22

Figure 23:
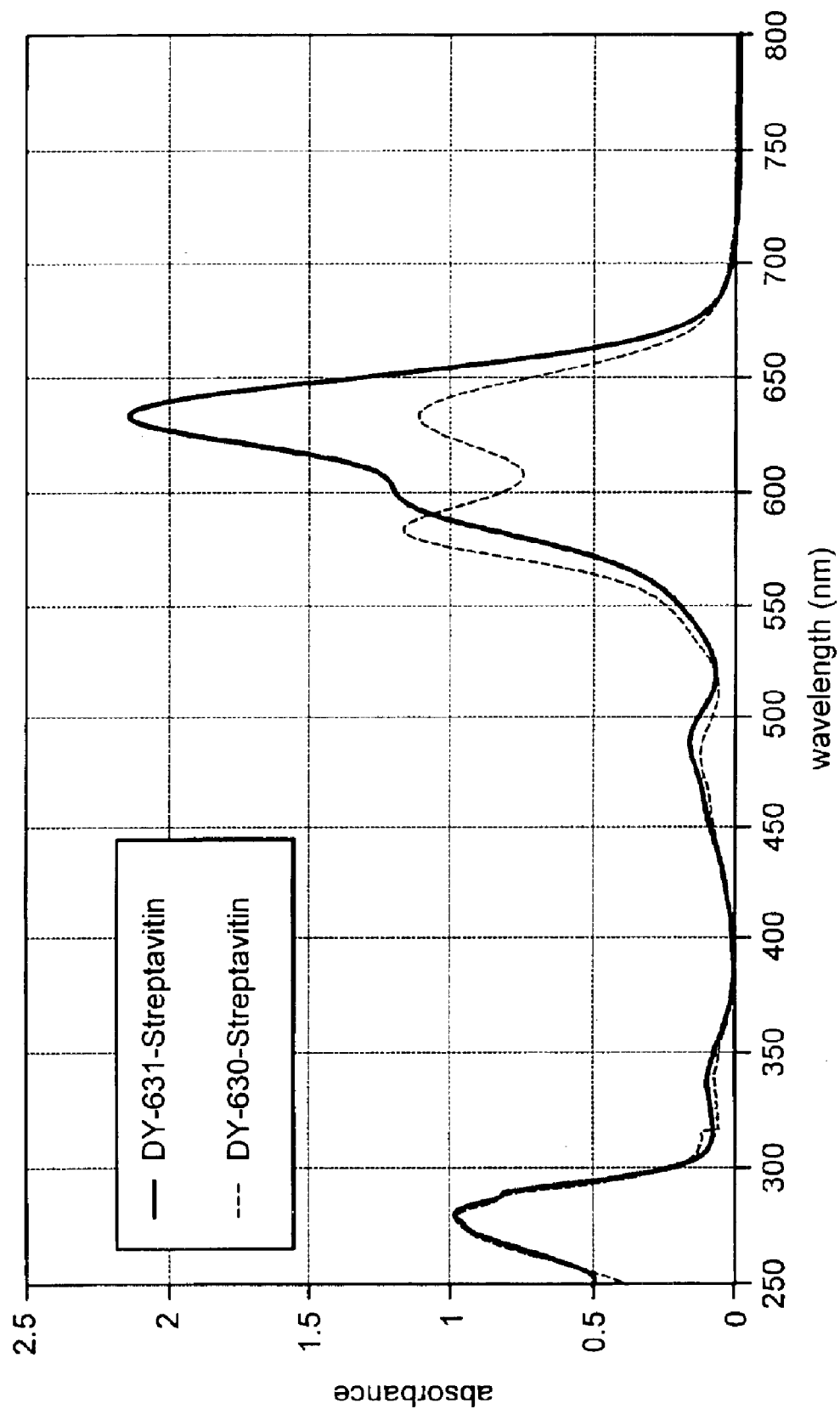

FIG. 23: Normalized UV-vis absorption spectra of two streptavidine conjugates obtained by reacting DY-630-NHS or DY-631-NHS esters with streptavidine in the molar ratio of 2:1. The advantage of the new markers is apparent from the reduced aggregation band for the DY-631 conjugate at 580 nm.

Figure 24:
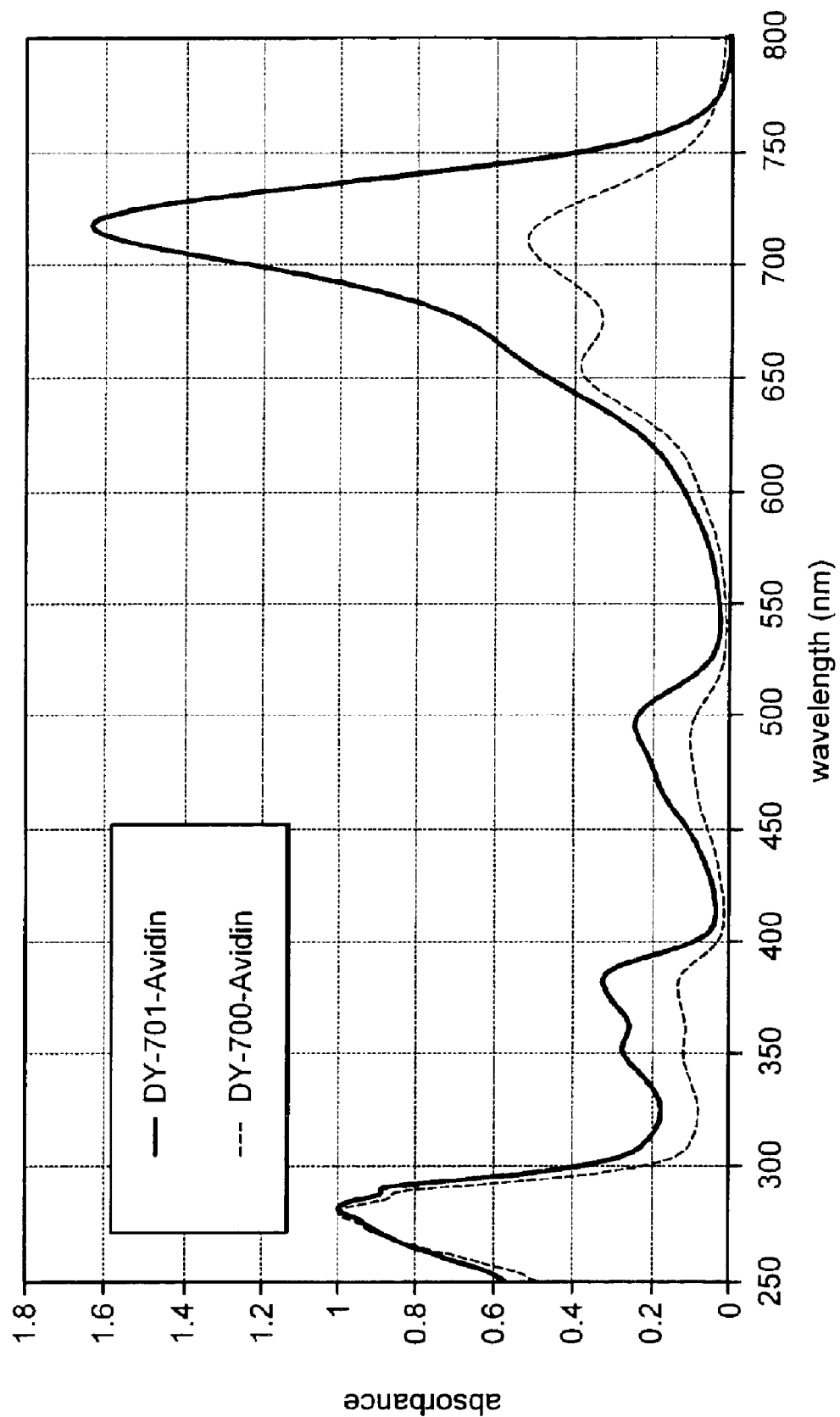

FIG. 24: Normalized UV-vis absorption spectra of two avidin conjugates obtained by reacting DY-700-NHS or DY-701-NHS esters with avidin in the molar ratio of 2:1. The advantage of the new markers is apparent from the reduced aggregation band for the DY-701 conjugate at 650 nm.

The concept of "vacuum" below refers to the 30–150 mbar pressure range. Liquid mixing ratios are by volume. RT denotes room temperature. NHS means N-Hydroxysuccinimide; DCC means Dicyclohexylcarbodiimide; DMF means N,N-Dimethylformamide.

EXAMPLES 1–16 (GENERAL FORMULA II COMPLEXES)

1. Synthesis of DY-631

180 mg (0.5 mmol) 2-tert-butyl-7-diethylamino-4-methyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt are dissolved in 50 ml of acetanhydride, with 75 µl (0,6 mmol) of trimethylorthoformate and 1 ml of pyridine. The solution is stirred for approx. 30 min at approx. 140° C. After cooling to RT, the solvent is removed in the vacuum.

The residue is heated to reflux for 2 hours in a mixture of 10 ml of acetone and 10 ml of 2 M hydrochloric acid, the reaction solution neutralized with $NaHCO_3$ and the solvent distilled in the vacuum. The residue is chromatographed ($SiO_2$—RP-18, eluent methanol/water—6:4).

145 mg (39%) yield–UV/Vis (ethanol) $\lambda_{max}$ ($\epsilon$)=637 nm (185.000 $l \cdot mol^{-1} \cdot cm^{-1}$).–fluorescence $\lambda_{em}$=658 nm.–MS (ESI$^-$): 713.2 [M]$^-$; 356.4 [M–H]$^{2-}$.–$C_{36}H_{45}N_2O_9S_2Na$ (736.88).

2. Synthesis of DY-631 N-Hydroxysuccinimidyl ester 15 mg DY-631, 14 mg DCC, 4 mg NHS and 10 µl pyridine are dissolved in 2 ml of DMF and stirred at RT for 24 h. The solvent is removed in vacuum. The residue is washed with diehtylether and dried in vacuum. The reaction is quantitative.

3. Synthesis of DY-636

206 mg (0.5 mmol) 10-tert-butyl-8-methyl-2,3,5,6-tetrahydro-1H,4H-11-oxonia-3a-aza-benzo[de]anthracene-tetrafluoroborate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

135 mg (36%) yield–UV/Vis (ethanol) $\lambda_{max}$ ($\epsilon$)=645 nm (155.000 $l \cdot mol^{-1} \cdot cm^{-1}$).–fluorescence $\lambda_{em}$=670 nm.–MS (ESI$^-$): 737.1 [M]$^-$; 368.4 [M–H]$^{2-}$.–$C_{38}H_{45}N_2O_9S_2Na$ (760.91).

4. Synthesis of DY-636 N-Hydroxysuccinimidyl ester 15 mg DY-636, 14 mg DCC and 4 mg NHS are reacted and processed in accordance with example 2.

5. Synthesis of DY-651

206 mg (0.5 mmol) 2-tert-butyl-8-ethyl-4,5,7,7-tetramethyl-7,8-dihydro-1-oxonia-8-aza-anthracene-tetrafluoroborate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

145 mg (38%) yield–UV/Vis (Ethanol) $\lambda_{max}$ ($\epsilon$)=653 nm (160.000 $l \cdot mol^{-1}$ $cm^{-1}$).–fluorescence $\lambda_{em}$=678 nm.–MS (ESI$^-$): 765.1 [M]$^-$; 382.4 [M–H]$^2$.–$C_{40}H_{49}N_2O_9S_{Na}$ (888.96).

6. Synthesis of DY-651 N-Hydroxysuccinimidyl ester 15 mg DY-651, 14 mg DCC and 4 mg NHS are reacted and processed in accordance with example 2.

7. Synthesis of DYQ-661

196 mg (0.5 mmol) 7-diethylamino-3,4-dimethyl-2-phenyl-chromenylium-tetra-fluoroborate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

145 mg (37%) yield–UV/Vis (Ethanol) $\lambda_{max}$ ($\epsilon$)=661 nm (116.000 $l \cdot mol^{-1}$ $cm^{-1}$).–MS (ESI$^-$): 747.1 [M]$^-$, 373.6 [M–H]$^{2-}$.–$C_{39}H_{43}N_2O_9S_2Na$ (770.90).

8. Synthesis of DYQ-661 N-Hydroxysuccinimidyl ester 15 mg DYQ-661, 14 mg DCC and 4 mg NHS are reacted and processed in accordance with example 2.

9. Synthesis of DY-676

216 mg (0.5 mmol) 8-ethyl-4,5,7,7-tetramethyl-2-phenyl-7,8-dihydro-1-oxonia-8-aza-anthracene-tetrafluoroborate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

150 mg (37%) yield–UV/Vis (Ethanol) $\lambda_{max}$ ($\epsilon$)=674 nm (84.000 l·mol$^{-1}$·cm$^{-1}$).–fluorescence $\lambda_{em}$=699 nm.–MS (ESI$^+$): 785.5 [M]$^+$.–$C_{42}H_{45}N_2O_9S_2Na$ (807.95).

10. Synthesis of DY-676 N-Hydroxysuccinimidyl ester 15 mg DY-676, 14 mg DCC and 4 mg NHS are reacted and processed in accordance with example 2.

11. Synthesis of DY-731

180 mg (0.5 mmol) 2-tert butyl-7-diethylamino-4-methyl-chromenylium-tetrafluoro-borate und 307 mg (0.5 mmol) 3-(3-ethoxycarbonylpropyl)-3-methyl-2-(4-phenyl-aminobuta-1,3-dienyl)-5-sulfonato-1-(3-sulfonatopropyl)-3H-indolium sodium salt are dissolved in 50 ml of acetanhydride with 1 ml of pyridine. The solution is stirred for approx. 30 min at approx. 140° C. After cooling to RT, the solvent is removed in the vacuum.

The residue is refluxed for 2 hours in a mixture of 10 ml acetone and 10 ml 2-M hydrochloric acid, the reaction solution neutralized with NaHCO$_3$ and the solvent distilled in the vacuum. The residue is chromatographed (SiO$_2$—RP-18, eluent methanol/water—6:4).

120 mg (31%) yield–UV/Vis (ethanol) $\lambda_{max}$ ($\epsilon$)=736 nm (225.000 l·mol$^{-1}$·cm$^{-1}$).–fluorescence $\lambda_{em}$=759 nm.–MS (ESI$^-$): 739.2 [M]$^-$, 369.5 [M–H]$^{2-}$.–$C_{38}H_{47}N_2O_9S_2Na$ (762.92).

12. Synthesis of DY-731 N-Hydroxysuccinimidyl ester 15 mg DY-731, 14 mg DCC and 4 mg NHS are reacted and processed in accordance with example 2.

13. Synthesis of DY-751

206 mg (0.5 mmol) 2-tert-butyl-8-ethyl-4,5,7,7-tetramethyl-7,8-dihydro-1-oxonia-8-aza-anthracene-tetrafluoroborate and 307 mg (0.5 mmol) 3-(3-ethoxycarbonylpropyl)-3-methyl-2-(4-phenyl-aminobuta-1,3-dienyl)-5-sulfonato-1-(3-sulfonatopropyl)-3H-indolium sodium salt are reacted and processed in accordance with example 11.

120 mg (29%) yield–UV/Vis (ethanol) $\lambda_{max}$ ($\epsilon$)=751 nm (220.000 l·mol$^{-1}$·cm$^{-1}$).–fluorescence $\lambda_{em}$=779 nm.–MS (ESI$^+$): 793.1 [M+H]$^+$, 419.4 [M+2 Na]$^{2+}$, 408.4 [M+H+Na]$^{2+}$, 397.4 [M+2 H]$^{2+}$.–$C_{42}H_{51}N_2O_9S_2Na$ (814.99).

14. Synthesis of DY-751 N-Hydroxysuccinimidyl ester 15 mg DY-751, 14 mg DCC and 4 mg NHS are reacted and processed in accordance with example 2.

15. Synthesis of DY-776

216 mg (0.5 mmol) 8-ethyl-4,5,7,7-tetramethyl-2-phenyl-7,8-dihydro-1-oxonia-8-aza-anthracene-tetrafluoroborate and 307 mg (0.5 mmol) 3-(3-ethoxycarbonylpropyl)-3-methyl-2-(4-phenylarnino-buta-1,3-dienyl)-5-sulfonato-1-(3-sulfonatopropyl)-3H-indolium sodium salt are reacted and processed in accordance with example 11.

110 mg (26%) yield–UV/Vis (Ethanol) $\lambda_{max}$ ($\epsilon$)=771 nm (147.000 l·mol$^{-1}$·cm$^{-1}$).–fluorescence $\lambda_{em}$=801 nm.–MS (ESI$^+$): 813.1 [M+H]$^+$, 429.2 [M+2 Na]$^{2+}$, 418.3 [M+H+Na]$^{2+}$, 407.3 [M+2 H]$^{2+}$.–$C_{44}H_{47}N_2O_9S_2Na$ (834.98).

16. Synthesis of DY-776 N-Hydroxysuccinimidyl ester 15 mg DY-776, 14 mg DCC and 4 mg NHS are reacted and processed in accordance with example 2.

EXAMPLES 17–22 (GENERAL FORMULA I COMPLEXES)

17. Synthesis of DY-681

180 mg (0.5 mmol) 4-tert-butyl-7-diethylamino-2-methyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

140 mg (39%) yield–UV/Vis (Ethanol) $\lambda_{max}$ ($\epsilon$)=691 nm (125.000 l·mol$^{-1}$·cm$^{-1}$).–fluorescence $\lambda_{em}$=708 nm.–MS (ESI$^-$): 713.2 [M]$^-$; 356.4 [M–H]$^{2-}$.–$C_{36}H_{45}N_2O_9S_2Na$ (736.88).

18. Synthesis of DY-681 N-Hydroxysuccinimidyl ester 15 mg DY-681, 14 mg DCC and 4 mg NHS are reacted and processed in accordance with example 2.

19. Synthesis of DY-701

196 mg (0.5 mmol) 7-diethylarnino-2,3-dimethyl-4-phenyl-chromenylium-tetrafluoro-borate and 242 mg (0.5 mmol) 3-(3-ethoxycarbonylpropyl)-2,3-dimethyl-5-sulfonato-1-(3-sulfonatopropyl)-3H-indolium sodium salt are reacted and processed in accordance with example 1.

150 mg (39%) yield–UV/Vis (Ethanol) $\lambda_{max}$ ($\epsilon$)=706 nm (115.000 l·mol$^{-1}$·cm$^{-1}$).–fluorescence $\lambda_{em}$=731 nm.–MS (ESI$^-$): 747.2 [M]$^-$; 373.4 [M–H]$^{2-}$.–$C_{39}H_{43}N_2O_9S_2Na$ (770.90).

20. Synthesis of DY-701 N-Hydroxysuccinimidyl ester 15 mg DY-701, 14 mg DCC and 4 mg NHS are reacted and processed in accordance with example 2.

21. Synthesis of DY-781

180 mg (0.5 mmol) 4-tert-butyl-7-diethylamino-2-methyl-chromenylium-tetrafluoro-borate and 307 mg (0.5 mmol) 3-(3-ethoxycarbonylpropyl)-3-methyl-2-(4-phenyl-aminobuta-1,3-dicnyl)-5-sulfonato-1-(3-sulfonatopropyl)-3H-indolium sodium salt are made to react and processed in accordance with example 11.

125 mg (33%) yield–UV/Vis (Ethanol) $\lambda_{max}$ ($\epsilon$)=783 nm (98.000 l·mol$^{-1}$·cm$^{-1}$).–fluorescence $\lambda_{em}$=800 nm.–MS (ESI$^+$): 785.3 [M+Na]$^+$; 763.3 [M+H]$^+$; 404.4 [M+2Na]$^{2+}$; 393.5 [M+H+Na]$^{2+}$.–$C_{38}H_{47}N_2O_9S_2Na$ (762.92).

22. Synthesis of DY-781 N-Hydroxysuccinimidyl ester 15 mg DY-781, 14 mg DCC and 4 mg NHS are reacted and processed in accordance with example 2.

What is claimed is:

1. An asymmetrical polymethine-based hydrophil marker of general structure Ia or IIa

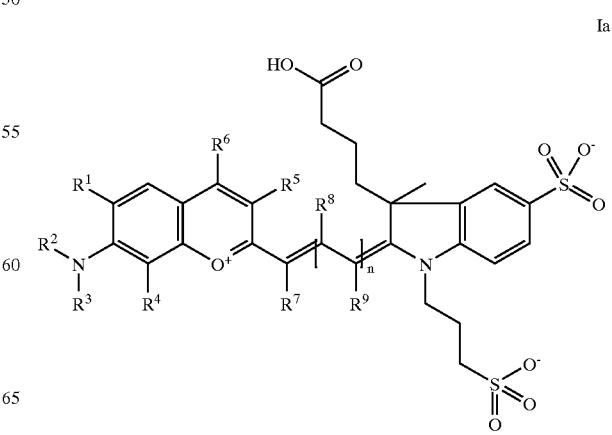

Ia

-continued

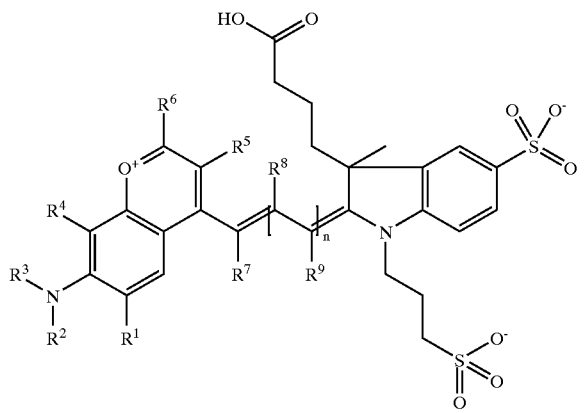

IIa where
- n stands for numerical values 0, 1, 2 or 3; substituents $R^8$ and $R^9$ occurring for n (doubled or threefold for n=2 or 3 respectively) may be the same or different,
- $R^1$–$R^9$ are the same or different and may be hydrogen, alkyl-, tert-alkyl, aryl-, carboxyaryl-, dicarboxyaryl, heteroaryl-, cycloalkyl-, heterocycloalkyl-, alkyloxy-, alkylmercapto- (with "alkyl" and "cycloalkyl" also including olefin linkage residues), aryloxy-, arylmercapto-, heteroaryloxy-, heteroarylmercapto-, hydroxy-, nitro- or cyano residues and $R^1$ and $R^2$, $R^2$ and $R^3$, $R^3$ and $R^4$, $R^5$ and $R^7$ can form one or more aliphatic, heteroaliphatic or aromatic rings,
- at least one or more of the $R^1$–$R^9$ substituents may constitute solubilizing or ionizing or ionized substituents, such as $SO_3^-$, $PO_3^{2-}$, $CO_2H$, OH, $NR_3^+$, cyclodextrins or sugars, which determine the hydrophil characteristics of dyes; these substituents may also be linked to the actual basic chromophore by means of an aliphatic or heteroaliphatic or cyclical spacer group,
- at least one of the $R^1$–$R^9$ substituents may stand for a reactive group permitting covalent linkage of the dye with another molecule, where the reactive group is selected from the group consisting of: isocyanates, isothiocyanates, hydrazines, amines, mono- and dichlor or mono- and dibromtriazines, aziridines, sulfonylhalogenides, N-hydroxysuccinimide esters, imido-esters, glyoxals or aldehydes for amin- and hydroxy functions or maleimides or iodacetamides for thiol functions and phosphoramidites for the marking of DNA or RNA or fractions thereof, and the reactive group is linked to the actual chromophore via an aliphatic or heteroaliphatic spacer group consisting of a structural element $[(CH_2)_a—Y—(CH_2)_b]_c—$, in which Y—the same or different—may be a $CR_2—$, O—, S—, $SO_2$, $SO_2NH—$, NR—, COO or CONR function, with R assuming the functions of $R^1$–$R^9$ and a and b—the same or different—representing values 0–18 and c values 1–18, and
- $R^6$ represents a substituent which, in a position relative to the pyran ring, displays a quartemary or $sp^2$-hybridized C atom; substituents $R^6$ and $R^5$ may also form an aliphatic or substituted aliphatic or aromatic ring system.

* * * * *